US010591486B2

(12) United States Patent
Pastre et al.

(10) Patent No.: US 10,591,486 B2
(45) Date of Patent: Mar. 17, 2020

(54) METHODS AND TOOLS FOR DETECTING INTERACTIONS IN EUKARYOTIC CELLS USING MICROTUBULE STRUCTURES AND DYNAMICS

(71) Applicants: INSTITUT NATIONAL DE LA SANTE ET DE LA RECHERCHE MEDICALE (INSERM), Paris (FR); UNIVERSITE D'EVRY—VAL D'ESSONNE, Evry (FR)

(72) Inventors: David Pastre, Evry (FR); Michel Cailleret, Evry (FR); Patrick Curmi, Evry (FR); Mirela Boca, Evry (FR)

(73) Assignees: INSTITUT NATIONAL DE LA SANTE ET DE LA RECHERCHE MEDICALE (INSERM), Paris (FR); UNIVERSITE D'EVRY — VAL D-ESSONNE, Evry (FR)

( * ) Notice: Subject to any disclaimer, the term of this patent is extended or adjusted under 35 U.S.C. 154(b) by 129 days.

(21) Appl. No.: 15/328,073

(22) PCT Filed: Jul. 21, 2015

(86) PCT No.: PCT/EP2015/066650
§ 371 (c)(1),
(2) Date: Jan. 23, 2017

(87) PCT Pub. No.: WO2016/012451
PCT Pub. Date: Jan. 28, 2016

(65) Prior Publication Data

US 2017/0242026 A1 Aug. 24, 2017

(30) Foreign Application Priority Data

Jul. 23, 2014 (EP) .................................... 14306190

(51) Int. Cl.

| | |
|---|---|
| ***G01N 33/68*** | (2006.01) |
| ***C12N 15/10*** | (2006.01) |
| ***C07K 14/47*** | (2006.01) |
| ***G01N 33/58*** | (2006.01) |

(52) U.S. Cl.
CPC ......... *G01N 33/6845* (2013.01); *C07K 14/47* (2013.01); *C12N 15/1055* (2013.01); *G01N 33/582* (2013.01); *C07K 2319/20* (2013.01); *C07K 2319/30* (2013.01); *C07K 2319/60* (2013.01); *C07K 2319/70* (2013.01); *G01N 2333/47* (2013.01)

(58) Field of Classification Search
CPC ........................ G01N 33/6845; C12N 15/1055
USPC ........................................................... 506/10
See application file for complete search history.

(56) References Cited

U.S. PATENT DOCUMENTS

| | | |
|---|---|---|
| 7,244,614 B2 | 7/2007 | Bright et al. |
| 2007/0706066 | 5/2007 | Cherkasky |
| 2008/0249058 A1 | 10/2008 | Roberson et al. |

FOREIGN PATENT DOCUMENTS

| | | |
|---|---|---|
| WO | 2000/017221 A1 | 3/2000 |
| WO | 00/50872 A2 | 8/2000 |
| WO | 2013/087921 A1 | 6/2013 |
| WO | 2014/064187 A1 | 5/2014 |

OTHER PUBLICATIONS

Lefevre et al., "Structural Basis for the Association of MAP6 Protein with Microtubules and Its Regulation by Calmodulin", Journal of Biological Chemistry, Aug. 23, 2013, pp. 24910-24922, vol. 288, No. 34.

Alba Abad et al., "Structural Basis for Microtubule Recognition by the Human Kinetochore Ska Complex", Nature Communications, Jan. 13, 2014, pp. 1-14, vol. 5.

Gomi et al., "MAP1B 1 126 Interacts with Tubulin Isoforms and Induces Neurite Outgrowth and Neuronal Death of Cultured Cortical Neurons", Brain Research, Nov. 11, 2011, pp. 1-8, vol. 1433.

Hristodorov et al., "EpCAM-Selective Elimination of Carcinoma Cells by a Novel MAP-Based Cytolytic Fusion Protein", Molecular Cancer Therapeutics, Jun. 30, 2014, pp. 2194-2202, vol. 13, No. 9.

Hristodorov et al., "Human Microtubule-Associated Protein Tau Mediates Targeted Killing of CD30 + Lymphoma Cells in Vitro and Inhibits Tumour Growth in Vivo", British Journal of Haematology, Jan. 25, 2014, pp. 251-257, vol. 164, No. 2.

Murga Penas et al., "A Novel Fusion of the MALT1 Gene and the Microtubule-Associated Protein 4 (MAP4) Gene Occurs in Diffuse Large B-Cell Lymphoma", Gene Chromosomes & Cancer, Jun. 27, 2006, vol. 45, No. 9.

Lowder et al., Visualizing protein partnerships in living cells and organisms. Curr Opin Chem Biol 15, 781-788, 2011.

(Continued)

*Primary Examiner* — Karla A Dines

(74) *Attorney, Agent, or Firm* — W&C IP

(57) ABSTRACT

A method for detecting an interaction between one or more protein bait and one or more candidate prey in a eukaryotic cell, comprising the steps of: a) providing an eukaryotic cell expressing (i) one or more protein bait, and (ii) one or more candidate prey, wherein said protein bait comprises a bait moiety and a polymerized-tubulin binding moiety. b) determining the occurence of an interaction between said one or more protein bait and said one or more candidate prey in the eukaryotic cell, wherein said protein bait is bound to polymerized tubulin in the eukaryotic cell, thereby localizing said one or more candidate prey along said polymerized tubulin, thereby detecting said interaction.

17 Claims, 8 Drawing Sheets

Specification includes a Sequence Listing.

(56) References Cited

OTHER PUBLICATIONS

Paul et al., Analyzing protein-protein interactions by quantitative mass spectrometry. Methods 54, 387-395, 2011.
Lee et al., Real-time single-molecule coimmunoprecipitation of weak protein-protein interactions. Nat Protoc 8, 2045-2060, 2013.
Jain et al., Probing cellular protein complexes using single-molecule pull-down. Nature 473, 484-488, 2011.
Lievens et al., Mammalian two-hybrids come of age. Trends Biochem Sci 34, 579-588, 2009.
Lam et al., Improving FRET dynamic range with bright green and red fluorescent proteins. Nat Methods 9, 1005-1012, 2012.
Roberson et al., "GSP:ATR94295", Oct. 9, 2008, Web.

(a) Transfection of cell samples (b) Basic fluorescence imaging (c) Detection

SEQUENCE LISTING

<160> NUMBER OF SEQ ID NOS: 14

<210> SEQ ID NO 1
<211> LENGTH: 250
<212> TYPE: PRT
<213> ORGANISM: Homo sapiens

<400> SEQUENCE: 1

Ile Ala Thr Pro Arg Gly Ala Ala Pro Pro Gly Gln Lys Gly Gln Ala
1 5 10 15

Asn Ala Thr Arg Ile Pro Ala Lys Thr Pro Pro Ala Pro Lys Thr Pro
20 25 30

Pro Ser Ser Gly Glu Pro Pro Lys Ser Gly Asp Arg Ser Gly Tyr Ser
35 40 45

Ser Pro Gly Ser Pro Gly Thr Pro Gly Ser Arg Ser Arg Thr Pro Ser
50 55 60

Leu Pro Thr Pro Pro Thr Arg Glu Pro Lys Lys Val Ala Val Val Arg
65 70 75 80

Thr Pro Pro Lys Ser Pro Ser Ser Ala Lys Ser Arg Leu Gln Thr Ala
85 90 95

Pro Val Pro Met Pro Asp Leu Lys Asn Val Lys Ser Lys Ile Gly Ser
100 105 110

Thr Glu Asn Leu Lys His Gln Pro Gly Gly Gly Lys Val Gln Ile Ile
115 120 125

Asn Lys Lys Leu Asp Leu Ser Asn Val Gln Ser Lys Cys Gly Ser Lys
130 135 140

Asp Asn Ile Lys His Val Pro Gly Gly Gly Ser Val Gln Ile Val Tyr

```
145                 150                 155                 160

Lys Pro Val Asp Leu Ser Lys Val Thr Ser Lys Cys Gly Ser Leu Gly
                165                 170                 175

Asn Ile His His Lys Pro Gly Gly Gly Gln Val Glu Val Lys Ser Glu
            180                 185                 190

Lys Leu Asp Phe Lys Asp Arg Val Gln Ser Lys Ile Gly Ser Leu Asp
        195                 200                 205

Asn Ile Thr His Val Pro Gly Gly Gly Asn Lys Lys Ile Glu Thr His
    210                 215                 220

Lys Leu Thr Phe Arg Glu Asn Ala Lys Ala Lys Thr Asp His Gly Ala
225                 230                 235                 240

Glu Ile Val Tyr Lys Ser Pro Val Val Ser
                245                 250


<210> SEQ ID NO 2
<211> LENGTH: 358
<212> TYPE: PRT
<213> ORGANISM: Homo sapiens

<400> SEQUENCE: 2

Gln Asn Lys Ile Leu Glu Gly Leu Glu Lys Leu Arg His Leu Asp Phe
1               5                   10                  15

Leu Arg Tyr Pro Val Ala Thr Gln Lys Asp Leu Ala Ser Gly Ala Val
            20                  25                  30

Pro Thr Asn Leu Lys Pro Ser Lys Ile Lys Gln Arg Ala Asp Ser Lys
        35                  40                  45

Glu Ser Leu Lys Ala Thr Thr Lys Thr Ala Val Ser Lys Leu Ala Lys
    50                  55                  60

Arg Glu Glu Val Val Glu Glu Gly Ala Lys Glu Ala Arg Ser Glu Leu
65                  70                  75                  80

Ala Lys Glu Leu Ala Lys Thr Glu Lys Lys Ala Lys Glu Ser Ser Glu
                85                  90                  95

Lys Pro Pro Glu Lys Pro Ala Lys Pro Glu Arg Val Lys Thr Glu Ser
            100                 105                 110

Ser Glu Ala Leu Lys Ala Glu Lys Arg Lys Leu Ile Lys Asp Lys Val
        115                 120                 125

Gly Lys Lys His Leu Lys Glu Lys Ile Ser Lys Leu Glu Glu Lys Lys
    130                 135                 140

Asp Lys Glu Lys Lys Glu Ile Lys Lys Glu Arg Lys Glu Leu Lys Lys
145                 150                 155                 160

Asp Glu Gly Arg Lys Glu Glu Lys Lys Asp Ala Lys Lys Glu Glu Lys
                165                 170                 175

Arg Lys Asp Thr Lys Pro Glu Leu Lys Lys Ile Ser Lys Pro Asp Leu
            180                 185                 190

Lys Pro Phe Thr Pro Glu Val Arg Lys Thr Leu Tyr Lys Ala Lys Val
        195                 200                 205

Pro Gly Arg Val Lys Ile Asp Arg Ser Arg Ala Ile Arg Gly Glu Lys
    210                 215                 220

Glu Leu Ser Ser Glu Pro Gln Thr Pro Pro Ala Gln Lys Gly Thr Val
225                 230                 235                 240

Pro Leu Pro Thr Ile Ser Gly His Arg Glu Leu Val Leu Ser Ser Pro
                245                 250                 255

Glu Asp Leu Thr Gln Asp Phe Glu Glu Met Lys Arg Glu Glu Arg Ala
            260                 265                 270
```

-continued

Leu Leu Ala Glu Gln Arg Asp Thr Gly Leu Gly Asp Lys Pro Phe Pro
275 280 285

Leu Asp Thr Ala Glu Glu Gly Pro Pro Ser Thr Ala Ile Gln Gly Thr
290 295 300

Pro Pro Ser Val Pro Gly Leu Gly Gln Glu Glu His Val Met Lys Glu
305 310 315 320

Lys Glu Leu Val Pro Glu Val Pro Glu Glu Gln Gly Ser Lys Asp Arg
325 330 335

Gly Leu Asp Ser Gly Ala Glu Thr Glu Glu Glu Lys Asp Thr Trp Glu
340 345 350

Glu Lys Lys Gln Arg Glu
355

<210> SEQ ID NO 3
<211> LENGTH: 308
<212> TYPE: PRT
<213> ORGANISM: Homo sapiens

<400> SEQUENCE: 3

Phe Lys Gln Ala Lys Asp Lys Val Ser Asp Gly Val Thr Lys Ser Pro
1 5 10 15

Glu Lys Arg Ser Ser Leu Pro Arg Pro Ser Ser Ile Leu Pro Pro Arg
20 25 30

Arg Gly Val Ser Gly Asp Arg Asp Glu Asn Ser Phe Ser Leu Asn Ser
35 40 45

Ser Ile Ser Ser Ser Ala Arg Arg Thr Thr Arg Ser Glu Pro Ile Arg
50 55 60

Arg Ala Gly Lys Ser Gly Thr Ser Thr Pro Thr Thr Pro Gly Ser Thr
65 70 75 80

Ala Ile Thr Pro Gly Thr Pro Pro Ser Tyr Ser Ser Arg Thr Pro Gly
85 90 95

Thr Pro Gly Thr Pro Ser Tyr Pro Arg Thr Pro His Thr Pro Gly Thr
100 105 110

Pro Lys Ser Ala Ile Leu Val Pro Ser Glu Lys Lys Val Ala Ile Ile
115 120 125

Arg Thr Pro Pro Lys Ser Pro Ala Thr Pro Lys Gln Leu Arg Leu Ile
130 135 140

Asn Gln Pro Leu Pro Asp Leu Lys Asn Val Lys Ser Lys Ile Gly Ser
145 150 155 160

Thr Asp Asn Ile Lys Tyr Gln Pro Lys Gly Gly Gln Val Gln Ile Val
165 170 175

Thr Lys Lys Ile Asp Leu Ser His Val Thr Ser Lys Cys Gly Ser Leu
180 185 190

Lys Asn Ile Arg His Arg Pro Gly Gly Gly Arg Val Lys Ile Glu Ser
195 200 205

Val Lys Leu Asp Phe Lys Glu Lys Ala Gln Ala Lys Val Gly Ser Leu
210 215 220

Asp Asn Ala His His Val Pro Gly Gly Gly Asn Val Lys Ile Asp Ser
225 230 235 240

Gln Lys Leu Asn Phe Arg Glu His Ala Lys Ala Arg Val Asp His Gly
245 250 255

Ala Glu Ile Ile Thr Gln Ser Pro Gly Arg Ser Ser Val Ala Ser Pro
260 265 270

Arg Arg Leu Ser Asn Val Ser Ser Ser Gly Ser Ile Asn Leu Leu Glu
275 280 285

```
Ser Pro Gln Leu Ala Thr Leu Ala Glu Asp Val Thr Ala Ala Leu Ala
    290                 295                 300

Lys Gln Gly Leu
305


<210> SEQ ID NO 4
<211> LENGTH: 162
<212> TYPE: PRT
<213> ORGANISM: Homo sapiens

<400> SEQUENCE: 4

Leu Ala Thr Asn Thr Ser Ala Pro Asp Leu Lys Asn Val Arg Ser Lys
1               5                   10                  15

Val Gly Ser Thr Glu Asn Ile Lys His Gln Pro Gly Gly Gly Arg Ala
            20                  25                  30

Lys Val Glu Lys Lys Thr Glu Ala Ala Ala Thr Thr Arg Lys Pro Glu
        35                  40                  45

Ser Asn Ala Val Thr Lys Thr Ala Gly Pro Ile Ala Ser Ala Gln Lys
    50                  55                  60

Gln Pro Ala Gly Lys Val Gln Ile Val Ser Lys Lys Val Ser Tyr Ser
65                  70                  75                  80

His Ile Gln Ser Lys Cys Gly Ser Lys Asp Asn Ile Lys His Val Pro
                85                  90                  95

Gly Gly Gly Asn Val Gln Ile Gln Asn Lys Lys Val Asp Ile Ser Lys
            100                 105                 110

Val Ser Ser Lys Cys Gly Ser Lys Ala Asn Ile Lys His Lys Pro Gly
        115                 120                 125

Gly Gly Asp Val Lys Ile Glu Ser Gln Lys Leu Asn Phe Lys Glu Lys
    130                 135                 140

Ala Gln Ala Lys Val Gly Ser Leu Asp Asn Val Gly His Leu Pro Ala
145                 150                 155                 160

Gly Gly


<210> SEQ ID NO 5
<211> LENGTH: 203
<212> TYPE: PRT
<213> ORGANISM: Homo sapiens

<400> SEQUENCE: 5

Ser Val Met Arg Gln Asp Tyr Arg Ala Trp Lys Val Gln Arg Pro Glu
1               5                   10                  15

Pro Ser Cys Arg Pro Arg Ser Glu Tyr Gln Pro Ser Asp Ala Pro Phe
            20                  25                  30

Glu Arg Glu Thr Gln Tyr Gln Lys Asp Phe Arg Ala Trp Pro Leu Pro
        35                  40                  45

Arg Arg Gly Asp His Pro Trp Ile Pro Lys Pro Val Gln Ile Ser Ala
    50                  55                  60

Ala Ser Gln Ala Ser Ala Pro Ile Leu Gly Ala Pro Lys Arg Arg Pro
65                  70                  75                  80

Gln Ser Gln Glu Arg Trp Pro Val Gln Ala Ala Ala Glu Ala Arg Glu
                85                  90                  95

Gln Glu Ala Ala Pro Gly Gly Ala Gly Gly Leu Ala Ala Gly Lys Ala
            100                 105                 110

Ser Gly Ala Asp Glu Arg Asp Thr Arg Arg Lys Ala Gly Pro Ala Trp
        115                 120                 125
```

```
Ile Val Arg Arg Ala Glu Gly Leu Gly His Glu Gln Thr Pro Leu Pro
    130                 135                 140

Ala Ala Gln Ala Gln Val Gln Ala Thr Gly Pro Glu Ala Gly Arg Gly
145                 150                 155                 160

Arg Ala Ala Ala Asp Ala Leu Asn Arg Gln Ile Arg Glu Glu Val Ala
                165                 170                 175

Ser Ala Val Ser Ser Ser Tyr Arg Asn Glu Phe Arg Ala Trp Thr Asp
            180                 185                 190

Ile Lys Pro Val Lys Pro Ile Lys Ala Lys Pro
        195                 200


<210> SEQ ID NO 6
<211> LENGTH: 145
<212> TYPE: PRT
<213> ORGANISM: Homo sapiens

<400> SEQUENCE: 6

Tyr Asp Pro Val Ala Ala Arg Gln Gly Gln Glu Thr Ala Val Ala Pro
1               5                   10                  15

Ser Leu Val Ala Pro Ala Leu Asn Lys Pro Lys Lys Pro Leu Thr Ser
            20                  25                  30

Ser Ser Ala Ala Pro Gln Arg Pro Ile Ser Thr Gln Arg Thr Ala Ala
        35                  40                  45

Ala Pro Lys Ala Gly Pro Gly Val Val Arg Lys Asn Pro Gly Val Gly
    50                  55                  60

Asn Gly Asp Asp Glu Ala Ala Glu Leu Met Gln Gln Val Asn Val Leu
65                  70                  75                  80

Lys Leu Thr Val Glu Asp Leu Glu Lys Glu Arg Asp Phe Tyr Phe Gly
                85                  90                  95

Lys Leu Arg Asn Ile Glu Leu Ile Cys Gln Glu Asn Glu Gly Glu Asn
            100                 105                 110

Asp Pro Val Leu Gln Arg Ile Val Asp Ile Leu Tyr Ala Thr Asp Glu
        115                 120                 125

Gly Phe Val Ile Pro Asp Glu Gly Gly Pro Gln Glu Glu Gln Glu Glu
    130                 135                 140

Tyr
145


<210> SEQ ID NO 7
<211> LENGTH: 451
<212> TYPE: PRT
<213> ORGANISM: Homo sapiens

<400> SEQUENCE: 7

Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Asn Thr Phe Phe Ser Glu Thr Gly Ala Gly Lys His Val Pro Arg
    50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95
```

-continued

```
Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
        115                 120                 125

Cys Thr Arg Leu Gln Gly Phe Leu Val Phe His Ser Phe Gly Gly Gly
    130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
        195                 200                 205

Ile Tyr Asp Ile Cys Arg Arg Asn Leu Asp Ile Glu Arg Pro Thr Tyr
    210                 215                 220

Thr Asn Leu Asn Arg Leu Ile Ser Gln Ile Val Ser Ser Ile Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Pro Leu Ala Thr Tyr
            260                 265                 270

Ala Pro Val Ile Ser Ala Glu Lys Ala Tyr His Glu Gln Leu Ser Val
        275                 280                 285

Ala Asp Ile Thr Asn Ala Cys Phe Glu Pro Ala Asn Gln Met Val Lys
    290                 295                 300

Cys Asp Pro Gly His Gly Lys Tyr Met Ala Cys Cys Leu Leu Tyr Arg
305                 310                 315                 320

Gly Asp Val Val Pro Lys Asp Val Asn Ala Ala Ile Ala Thr Ile Lys
                325                 330                 335

Thr Lys Arg Thr Ile Gln Phe Val Asp Trp Cys Pro Thr Gly Phe Lys
            340                 345                 350

Val Gly Ile Asn Tyr Gln Pro Pro Thr Val Val Pro Gly Gly Asp Leu
        355                 360                 365

Ala Lys Val Gln Arg Ala Val Cys Met Leu Ser Asn Thr Thr Ala Ile
    370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Met Ala Ala Leu Glu Lys Asp Tyr
            420                 425                 430

Glu Glu Val Gly Val Asp Ser Val Glu Gly Glu Gly Glu Glu Glu Gly
        435                 440                 445

Glu Glu Tyr
    450


<210> SEQ ID NO 8
<211> LENGTH: 444
<212> TYPE: PRT
<213> ORGANISM: Homo sapiens

<400> SEQUENCE: 8

Met Arg Glu Ile Val His Ile Gln Ala Gly Gln Cys Gly Asn Gln Ile
1               5                   10                  15
```

-continued

```
Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
        35                  40                  45

Val Tyr Tyr Asn Glu Ala Thr Gly Gly Lys Tyr Val Pro Arg Ala Ile
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Arg Leu Thr Thr Pro Thr Tyr Gly Asp
    210                 215                 220

Leu Asn His Leu Val Ser Gly Thr Met Glu Cys Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Asp
        275                 280                 285

Leu Thr Gln Gln Val Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ala Val Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430
```

-continued

```
Glu Glu Asp Phe Gly Glu Glu Ala Glu Glu Glu Ala
        435                 440


<210> SEQ ID NO 9
<211> LENGTH: 150
<212> TYPE: PRT
<213> ORGANISM: Homo sapiens

<400> SEQUENCE: 9

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys
145                 150


<210> SEQ ID NO 10
<211> LENGTH: 441
<212> TYPE: PRT
<213> ORGANISM: Homo sapiens

<400> SEQUENCE: 10

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160
```

-continued

```
Gly Gln Lys Gly Gln Ala Asn Ala Thr Arg Ile Pro Ala Lys Thr Pro
            165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440


<210> SEQ ID NO 11
<211> LENGTH: 32
<212> TYPE: PRT
<213> ORGANISM: Homo sapiens

<400> SEQUENCE: 11

Leu Gln Thr Ala Pro Val Pro Met Pro Asp Leu Lys Asn Val Lys Ser
1               5                   10                  15

Lys Ile Gly Ser Thr Glu Asn Leu Lys His Gln Pro Gly Gly Gly Lys
            20                  25                  30


<210> SEQ ID NO 12
<211> LENGTH: 31
<212> TYPE: PRT
<213> ORGANISM: Homo sapiens

<400> SEQUENCE: 12

Val Gln Ile Ile Asn Lys Lys Leu Asp Leu Ser Asn Val Gln Ser Lys
1               5                   10                  15
```

-continued

```
Cys Gly Ser Lys Asp Asn Ile Lys His Val Pro Gly Gly Gly Ser
            20                  25                  30


<210> SEQ ID NO 13
<211> LENGTH: 31
<212> TYPE: PRT
<213> ORGANISM: Homo sapiens

<400> SEQUENCE: 13

Val Gln Ile Val Tyr Lys Pro Val Asp Leu Ser Lys Val Thr Ser Lys
1               5                   10                  15

Cys Gly Ser Leu Gly Asn Ile His His Lys Pro Gly Gly Gly Gln
            20                  25                  30


<210> SEQ ID NO 14
<211> LENGTH: 32
<212> TYPE: PRT
<213> ORGANISM: Homo sapiens

<400> SEQUENCE: 14

Val Glu Val Lys Ser Glu Lys Leu Asp Phe Lys Asp Arg Val Gln Ser
1               5                   10                  15

Lys Ile Gly Ser Leu Asp Asn Ile Thr His Val Pro Gly Gly Gly Asn
            20                  25                  30
```

METHODS AND TOOLS FOR DETECTING INTERACTIONS IN EUKARYOTIC CELLS USING MICROTUBULE STRUCTURES AND DYNAMICS

FIELD OF THE INVENTION

The invention relates to methods, uses and tools for studying ligand interactions in an eukaryotic cell.

BACKGROUND OF THE INVENTION

The function of a number of proteins remains elusive, which slows down understanding of fundamental aspects of cell mechanisms and impedes advance in diagnostic and treatment of many diseases and in personalized medicine. One of the main obstacles to better understand a given protein's functions is that proteins generally interact with many other partners (proteins, nucleic acids, sugars, lipids . . . ) and many of these interactions are weak and transient, albeit of critical importance.

A series of methods have been developed to provide a better view on protein interaction (Lowder et al., Visualizing protein partnerships in living cells and organisms. Curr Opin Chem Biol 15, 781-788, 2011), among them immuno-precipitation assays, two-hybrid systems and variants like substrate complementation systems, Fluorescence Energy Transfer (FRET) or related techniques.

A typical procedure adopted by scientists is to take advantage of the high throughput capability of the two hybrid system, generally in yeast, to obtain an exhaustive list of potential partners for a protein of interest and then to control whether the proposed interactions are also detected with one of the two other methods (immuno-precipitation assays or FRET).

Each of these methods suffers from numerous drawbacks. Immuno-precipitation assays require cell lysis (Paul et al., Analyzing protein-protein interactions by quantitative mass spectrometry. Methods 54, 387-395, 2011), specific antibodies and adsorption onto non physiological substrates leading to false positives and false negatives. In addition, information obtained does not reflect necessary what may happen in living cells and most critically these methods detect strong interactions, even though some improvements have been done on this point (Lee et al., Real-time single-molecule coimmunoprecipitation of weak protein-protein interactions. Nat Protoc 8, 2045-2060, 2013) (Jain et al., Probing cellular protein complexes using single-molecule pull-down. Nature 473, 484-488, 2011). Two-hybrid systems can detect protein interactions in living cells but require two or more chimeric proteins and are unable to monitor rapid biochemical events taking place in the cells (Lievens et al., Mammalian two-hybrids come of age. Trends Biochem Sci 34, 579-588, 2009). In addition, weak and transient interactions are not detected. FRET can also detect protein interactions in living cells but the FRET signal is strongly dependent on the distance and the orientation of the donor and acceptor labels placed on the bait and target proteins, respectively. The detection of weak interactions is also challenging due to the low signal to noise ratio (Lam et al., Improving FRET dynamic range with bright green and red fluorescent proteins. Nat Methods 9, 1005-1012, 2012). In addition, when the bait and prey interact with each other but the donor is well separated from the acceptor (>4-5 nm), the FRET signal is weak.

Engineered fluorescent proteins suitable for FRET are further taught in WO 2013087921A1, such as pairs of donor and acceptor fluorescent proteins. Other alternatives to the yeast two-hybrid system, but distinct from FRET, have been developed for eukaryotic cells.

U.S. Pat. No. 7,244,614B2 teaches recombinant fusion proteins for detecting the binding of a molecule of interest, comprising a detection domain, a binding domain, and a localization domain such as a Nuclear Localization Signal (NLS) or a Nuclear Export Signal (NES).

WO 2000017221A1 relates to a method for measuring protein-protein interactions in living cells, using a first heterologous conjugate with a detectable group and a second heterologous conjugate that binds to an internal structure within said cells. According to WO 2000017221A1, an <<internal structure>> includes any non-uniformly distributed cellular component, including for instance proteins, lipids, carbohydrates, nucleic acids and derivatives thereof.

However there remains a need for novel methods and tools suitable for detecting weak and transient interactions between ligands in living cells.

There also remains a need for such methods which remain, at the same time, suitable for high-throughput screening.

There also remains a need for methods which provide suitable and physiological conditions in the context of a living cell, and which also remain suitable for the detection of ligand interactions in real-time.

SUMMARY OF THE INVENTION

The present invention relates to methods for identifying partners of ligands, such as proteins, in an eukaryotic cell, and more particularly in a living eukaryotic cell context. The system consists of an easy detection system based on the expression in cells of (i) a "bait", a known protein, which is brought to microtubules thanks to its fusion to a microtubule-binding domain and (ii) a prey which can be for instance a protein/polypeptide or a nucleic acid.

Surprisingly, it has been found that the prey, when interacting with the bait, becomes also localized along microtubules which makes it thus easily detectable. The invention presents the following advantages: (i) a high sensitivity protein partners detection system which can be automatized and which is thus suitable to high throughput methods. (ii) the detection of bait/prey interaction is performed in a living cell environment which preserves any post-translationnal modifications of the partners.

Thus, the invention relates to methods for detecting an interaction between one or more protein bait and one or more candidate prey in an eukaryotic cell.

The invention also relates to the use of a polymerized-tubulin binding moiety, such as a Microtubule-Binding Domain (MBD), fused to one or more bait, as a tool for determining the occurence of an interaction between said one or more bait and one or more candidate prey in an eukaryotic cell. The invention further relates to protein baits, vectors, cell lines and kits suitable for said methods and uses.

Thus, a first aspect of the invention is to provide a method for detecting an interaction between one or more protein bait and one or more candidate prey in an eukaryotic cell, comprising the steps of:

a) providing an eukaryotic cell expressing (i) one or more protein bait, and (ii) one or more candidate prey, wherein said protein bait comprises a bait moiety and a polymerized-tubulin binding moiety.

b) determining the occurence of an interaction between the said one or more protein bait and the said one or more candidate prey in the eukaryotic cell, wherein the said protein bait is bound to polymerized tubulin in the eukaryotic cell. Said protein bait is bound to polymerized tubulin in the eukaryotic cell, thereby localizing said one or more candidate prey along said polymerized tubulin, thereby detecting said interaction.

A second aspect of the invention relates to the use of a polymerized-tubulin binding moiety fused to one or more bait, as a tool for determining the occurence of an interaction between said one or more bait and one or more candidate prey in an eukaryotic cell. Said protein bait is bound to polymerized tubulin in the eukaryotic cell, thereby localizing said one or more candidate prey along said polymerized tubulin, thereby detecting said interaction.

A third aspect of the invention relates to a protein bait comprising a polymerized-tubulin binding moiety comprising one or more Microtubule-Binding Domain(s), and a bait moiety.

A fourth aspect of the invention relates to a vector containing an expression cassette suitable for expressing a protein bait of the invention.

A fifth aspect of the invention relates to cell lines that are transfected with a vector of the invention, and/or that stably express a protein bait of the invention.

A sixth aspect of the invention relates to kits for detecting an interaction of one or more protein bait with one or more candidate prey in a cell, comprising a protein bait, a vector, and/or a cell line of the invention.

DETAILED DESCRIPTION OF THE INVENTION

Figure 1:
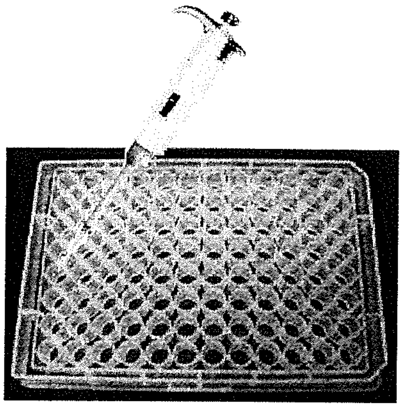
FIG. 1: Principle of the method: high throughput analysis and detection system. Application to an endogenous mRNA interaction with YB-1, a mRNA-binding protein. (A) cells cultivated on microplates are transfected by an automate system. (B) after image acquisition, the identification of a “microtubule-like pattern” in the fluorescence channel corresponding to the prey (messenger RNA) certifies the interaction between the bait (YB-1-GFP-tau) and the prey (mRNA). (C) (upper panel; from left to right) Detection of the bait: YB-1-GFP-Tau; Detection of the prey: mRNA; Example of the detection of a protein-RNA interaction showing the presence of a microtubule-like pattern in the Cy3 channel (corresponding to the Poly-T RNA Cy3-labeled probe to detect mRNA). (lower panel) YB-1-GFP is used as a control and is homogenously distributed in the cytoplasm.
Figure 1:
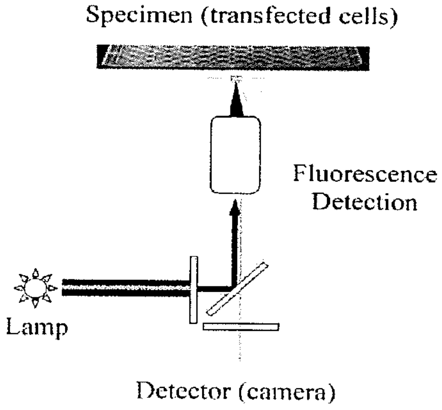
Figure 1:
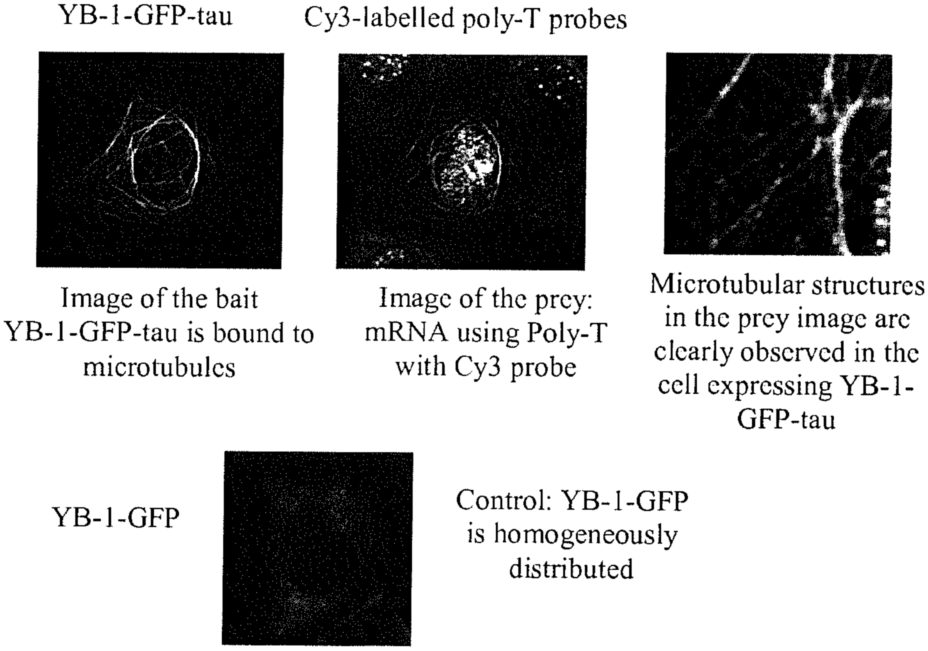

The invention relates to methods for detecting an interaction between one or more protein bait and one or more candidate prey in an eukaryotic cell.

According to the invention, a “protein bait” comprises at least one “bait moiety” and at least one “polymerized-tubulin binding moiety”.

According to one embodiment, said “protein bait” comprises at least one “bait moiety” and at least one “polymerized-tubulin binding moiety” which are not from a same naturally-occuring protein.

According to the invention, the expression “comprising” or “comprises” also includes “consisting” or “consisting of”.

A “bait moiety” is a moiety which is prone to interact with one or more candidate prey(s) in the cell.

A “polymerized-tubulin binding moiety” comprises a peptide, a protein, or a nucleoprotein which has the ability to bind specifically to polymerized tubulin. Preferably, the “polymerized-tubulin binding moiety” binds with a higher specificity to tubulin in its polymeric form than to tubulin in its non-polymeric form, which includes its monomeric form and/or its heterodimeric form (which corresponds to the alpha/beta tubulin heterodimer). Ideally, a polymerized-tubulin binding moiety binds mostly or even exclusively to polymerized-tubulin, which includes microtubules.

Microtubules are a component of the cytoskeleton, found throughout the cytoplasm. Microtubules are part of a structural network (the "cytoskeleton") within the cell's cytoplasm. The primary role of the microtubule cytoskeleton is mechanical support, although microtubules also take part in many other processes. Thus, microtubules are only part of the so-called "microtubule cytoskeleton", because the latter further includes associated proteins, such as Microtubule-Associated Proteins (MAPs) along with other organizing structures such as the centrosomes.

"Polymerized tubulin" or "Polymerized-tubulin" refers exclusively to the assembly of monomeric tubulin, or alternatively of the assembly of heterodimers of tubulin, in a regular fashion and with a distinct polarity.

Tubular polymers of tubulin can grow as long as 50 micrometres, with an average length of 25 μm, and are highly dynamic. The outer diameter of a microtubule is generally of about 24-25 nm while the inner diameter is of about 12 nm. They are found in eukaryotic cells and are formed by the polymerization of a dimer of two globular proteins, α-tubulin and β-tubulin. Thus, the expression "polymerized tubulin" encompasses microtubules.

Thus, "microtubules" represent a particular rearrangement of "polymerized tubulin", which occurs physiologically in eukaryotic cells, and which forms with additional partners the "microtubule cytoskeleton". The physiological assembly of microtubules is generally described as comprising a first step of regulated assembly of alpha-tubulin and beta-tubulin heterodimers, which together form a polarized protofilament. Then, protofilaments are believed to assemble, as a cylinder, into the so-called microtubule. Thus, microtubules are generally described as polymers of dimers of α- and β-tubulin, which are composed of 13 protofilaments assembled around a hollow core. However, it shall be noted that so-called microtubules with a different number of protofilaments have also been described in the Art, such as microtubules with 14 or 15 protofilaments. However, the physiological meaning of such variations, or "protofilament transitions", remains unclear.

The man skilled in the Art knows that tubulin is one of several members of a small family of globular proteins. The tubulin superfamily includes five distinct families, the alpha-, beta-, gamma-, delta-, and epsilon-tubulins and a sixth family (zeta-tubulin) which is present only in kinetoplastid protozoa. The most common members of the tubulin family are alpha-tubulin (α-tubulin) and beta-tubulin (β-tubulin), the proteins that make up microtubules. The end of the microtubule which corresponds to beta-tubulin is called the plus-end. The end of the microtubule which corresponds to alpha-tubulin is called the minus-end.

Thus, a "polymerized-tubulin binding moiety" of the invention may include an alpha-tubulin and/or a beta-tubulin binding moiety and/or combinations thereof, and binds preferably to tubulin in its polymeric form rather than its monomeric form or its heterodimeric form.

As known in the Art, the "heterodimeric form" of tubulin corresponds to the alpha/beta tubulin heterodimer. Thus, the polymeric form of tubulin also corresponds to a polymer of heterodimers, which also corresponds to more than one heterodimer of alpha/beta tubulin.

For reference, human alpha-tubulin is of sequence SEQ ID N°7.

For reference, human beta-tubulin is of sequence SEQ ID N°8.

Without wishing to be bound by the theory, the inventors are of the opinion that polymerized tubulin, and more particularly the microtubule surface, is a unique active platform which provides previously unrecognized properties for screening ligand interactions in an eukaryotic cell.

First, microtubules offer a large surface within the cell owing to their dimensions (25 nm in diameter and tenth of micrometers in length). If we consider one hundred 10 μm-long microtubules in typical mammalian cells like HeLa cells, the microtubule surface is larger than 30 $\mu m^2$ and can even be larger in cells like neurons or muscle cells. Thus, such large surface is available for the binding of an enormous number of baits without saturation (if the bait requires an interacting surface as large as 10 $nm^2$ on microtubules, virtually, more than 3 000 000 bait copies per cell can theoretically be anchored to microtubules). This is significantly higher than the typical number of over-expressed proteins in transfected mammalian cells (about 100 000 copies is already a large over-expression for most proteins).

A second advantage of using the microtubule surface lies in its dynamic behavior. Microtubules are intrinsically highly dynamics and alternate permanently between shortening and growing phases. This behavior allows to dissociate the bait from microtubules during the depolymerization phase and to bind to another microtubule or after repolymerization of the microtubule. During that interval of time, the bait moves away from microtubules and is then able to capture preys that are located in the bulk cytoplasm and not at the vicinity of microtubules. Microtubule-disrupting or Microtubule-depolymerizing drugs, such as Nocodazole, Vinblastine, Vincristine, Colchicine, Colcemid, Podophyllotoxin, Rizhoxin or Vinorelbine, can also be used for that purpose.

Baits can be brought to microtubules using a fused polymerized-tubulin binding moiety, such as Microtubule-Associated Proteins (MAPs) including tau (NCBI Reference Sequence: NP_005901.2), or Microtubule-Binding Domains (MBD).

According to one embodiment, the anchoring of the bait is due to the repetition of Microtubule-Binding Domains generally present in MAPs. These repeats have a high affinity toward microtubules compared to free tubulin, the building block of microtubules, and only a weak portion will be free in the cell cytoplasm using this method.

When the prey interacts with the bait brought to microtubules, its relocation on microtubule surface allows its detection via the appearance of microtubular structures in the prey's fluorescent image.

It has been known for a long time that the detection of filamentous structures, such as "microtubule-like patterns" is highly sensitive and consists in extrapolating a straight line in the fluorescence image so that the signal can be detected out of a homogenously-distributed noise. This general principle is routinely used to image microtubules by fluorescence speckle microscopy (for a review, see Salmon & Waterman; How we discovered fluorescent speckle microscopy; Mol Biol Cell, 3940-2; 2011).

However, this easy detection method would not be possible in more globular structure or other improperly defined substrate. Methods of the invention are also compatible with Real-time data analysis of the living cell fluorescent images, and thus can be implemented to better detect the bait bound to microtubules in living cells. The point is that the microtubules are moving with time due to their highly dynamical structures, which further improves their detection out of large fluorescent background for the detection in living cells.

For all these reasons, the choice of microtubules is highly relevant, even compared to other kinds of filaments. As the interaction between the bait and the prey can be observed in real time, transient interactions occurring for example after post-translational modification like phosphorylation events can be observed in real time.

Such method is also particularly efficient for studying the effect of mutations in the interaction of a given bait to a candidate prey.

In other words, the inventors now propose that polymerized tubulin, and by extension polymerized-tubulin binding moieties, can be used as tools for detecting an interaction between one or more protein bait and one or more candidate prey in an eukaryotic cell. Thus, this represents a "paradigm shift" as microtubules were mostly known, so far, as an object of study in itself, but not as a tool for detecting ligand interactions in an eukaryotic cell.

Because it relies on microtubule structure in fixed or living cells and microtubule dynamics in living cells, this method also represents an alternative to the two widely used methods to probe protein interactions in living cells: (i) FRET between a donor fused to a bait and an acceptor fused to the prey and (ii) the two hybrid system relying on fragment complementation or proteins fused to the bait and the prey which reconstitution generates a quantifiable signal (for example β-galactosidase assay):

(i) Compared to FRET, this method is easier to handle, because one has simply to co-transfect cell and to observe whether or not microtubule structures appear after cells transfection using the fluorescence signal of the prey. Our detection scheme is independent of the distance between the prey and the bait and the fluorescent signal detected along microtubules is directly proportional to the amount of prey interacting with the bait on microtubules. FRET detection is more demanding since both the distance between the fluorescent labels and their relative orientation when the prey and the bait are interacting strongly modulate the FRET signal intensity. This is why the widespread application of FRET is limited. As a result, a case-by-case optimization is often required. In addition, a costly experimentation and good expertise are necessary for the detection of the FRET signal. The alternative BIFC (bimolecular fluorescent complementation) cannot allow the analysis of dynamical interaction and suffers from the possibility that the interaction between bait and the prey is biased by stable complementation.

(ii) The two hybrid system and especially the yeast two hybrid (Y2H) technique is the most widely used method because of its high throughput for mapping static interactions. However, compared to two hybrid assays, our method allows the detection of protein interactions in real time and, thus, allows to capture the plasticity of protein interactions. The physiological context in which the interactions take place is also questionable in Y2H experiments, which is not the case in the claimed methods. In that respect, the method of the invention can be complementary to Y2H since it can easily decipher whether or not the bait and the prey interact in mammalian cells. High throughput can also be implemented using the claimed method like in Y2H since arrays of cell samples can be analyzed by video-microscopy for living cells or by classical microscopy for fixed cells. Lastly, in the Y2H method, both the bait and the prey are fused to the necessary adaptation proteins, which can then be coalesced to form a functional complex. In our methods, the prey can be free (antibody detection in fixed cells), labeled with small non-fluorescent tag like FLAG or V5 or a simple fluorescent-tag like GFP used for living cell experiments.

Methods and uses of the invention have been further validated, as shown from the examples. Briefly, a plasmid has been designed to direct the expression of a known protein (bait) fused to the tau protein via its N-terminal domain (end of the projection domain of tau) in mammalian cells.

After being fused to tau, two baits were successfully brought to microtubules: eIF2B (translation initiation factor eIF-2B subunit epsilon; Accession Number: NP_003898.2), a translation initiation factor, and YB-1 (nuclease-sensitive element-binding protein 1 or Y-box binding protein; Accession Number: NP_004550.2), a mRNA-binding protein, have both been easily detected along microtubules by optical microscopy in NRK or HeLa cells (normal rat epithelial and human cancer cells respectively).

In living cells, fluorescence video-microscopy analysis using GFP-labeled YB-1 or eIF2B as bait revealed the interaction of YB-1 with itself as well as the binding eIF2A to eIF2B but only after arsenite treatment, which induces the phosphorylation of eIF2A (Accession Number: NP_114414.2). This is evidence that the method is perfectly suitable to study the effect of post-translational modifications. In the case of eIF2A (eukaryotic translation initiation factor 2A), its phosphorylation is an early event occurring after various environmental stresses in mammalian cells, which leads to translation arrest. Such strategy could be useful for stress detection in living cells (reporter cells).

Using YB-1 as bait, in situ hybridization with cy3-labelled poly-T probes (40 nucleotides) revealed the presence of mRNA brought to microtubules, in agreement with the fact that YB-1 is a known mRNA binding protein. This method is therefore also suitable to probe protein-RNA interaction in the cellular context including miRNA, mRNA, rRNA and tRNA.

The "bait moiety" and the candidate prey may be identical or different, and are preferably selected in a group comprising (or consisting in) a protein or a nucleic acid, which includes nucleoproteins.

In a non-limitative manner, a "bait moiety" and/or a "candidate prey" includes any molecule of interest, particularly proteins of interest, such as antibodies, nucleic-acid binding proteins and various other bait receptor proteins or peptides, notably those of biological relevance, including those of diagnostic and pharmacological relevance.

It also includes nucleic acids, such as messenger RNAs, coding and non-coding RNAs, transfert RNAs, ribosomal RNAs, interfering RNAs or silencing RNAs.

The interaction between the bait and the prey is assessed due to the interaction of the protein bait to polymerized tubulin by a polymerized-tubulin binding moiety. Thus, it is preferable that said bait moiety does not interact or colocalize at all with polymerized tubulin, or in a limited manner, when compared to the same moiety conjugated to the polymerized tubulin binding moiety under reference and/or physiological conditions.

Bait moieties which are particularly considered are bait moieties of which the distribution is diffuse in the cytoplasm of the eukaryotic cell under reference and/or physiological conditions.

A "physiological" condition may consist of an experimental set-up in which the eukaryotic cell is not in a situation of stress, or apoptosis, which includes an experimental set-up in which the eukaryotic cell is not in contact with a medium having a non-physiological pH, or salt condition.

According to some embodiments, the "bait moiety" is a moiety that does not interact, or co-localize, with polymerized tubulin (or microtubules) in the eukaryotic cell under reference or physiological conditions.

According to one exemplary embodiment a "bait moiety" is a nucleic-acid binding moiety, such as a nucleic-acid binding protein, and a "candidate prey" is a nucleic acid, such as a messenger RNA.

According to another embodiment, a "bait moiety" is an antibody or a fragment thereof, and a "candidate prey" is a protein or a peptide that is susceptible to bind to said antibody.

According to another embodiment, a "bait moiety" is a nucleic acid, such as a messenger RNA, and a "candidate prey" is a nucleic-acid binding moiety, such as a nucleic-acid binding protein.

A "candidate prey" can be a native or modified, homologous or heterologous candidate prey.

The "polymerized-tubulin binding moiety" can be ideally chosen among known antibodies, microtubule-binding proteins, or fragments thereof, which includes (in a non-exhaustive manner) microtubule stabilizers and destabilizers, molecular motors, microtubule-severing proteins and end-tracking proteins such as plus-end tracking proteins.

For reference, a list of microtubule-binding proteins is provided herebelow:

TABLE 1 list of microtubule-binding proteins

| Function | Protein name or family |
|---|---|
| Microtubule Stabilizers | MAP1 family |
| | Microtubule-associated protein 1A |
| | Microtubule-associated protein 1B |
| | Microtubule associated proteins 1A/1B light chain 3A |
| | Microtubule associated proteins 1A/1B light chain 3B |
| | MAP RP/EB family |
| | Microtubule-associated protein RP/EB family member 1 |
| | Microtubule-associated protein RP/EB family member 2 |
| | Microtubule-associated protein RP/EB family member 3 |
| | WD repeat EMAP family |
| | Cytoskeleton-associated protein 5 (Dis1/Tog) |
| | Ferritin heavy chain (Syncolin) |
| | MAP7 domain-containing protein 1 |
| | Microtubule-associated protein 2 |
| | Microtubule-associated protein 4 |
| | Microtubule-associated protein 7 |
| | Microtubule-associated protein tau |
| | STOP (MAP6) |
| Destabilizers | Kinesin-like protein KIF2A (Kinesin-2) |
| | Stathmin (Op18, prosolin, metablastin) |
| Molecular motors | Cytoplasmic dyneins & dynactin |
| | Kinesins |
| Severing | Katanin |
| | Spastin |
| Plus-end tracking proteins | Cytoplasmic linker proteins (CLIPs): CLIP-170, CLIP-115, CLIP-190 |
| | CLIPs associating proteins (CLASPs): CLASP1, CLASP2, MAST/Orbit |
| | MCAK (mitotic centromere-associated kinesin) |
| | XMAP215, dCP224 |
| | EB/PR family proteins: EB-1, EB-2, EB-3, RP1, Bim1p, Mal3p |
| | Cytoplasmic linker proteins (CLIPs): CLIP-170, CLIP-115, CLIP-190 |
| | Gephyrin |

Thus, the "polymerized-tubulin binding moiety" may be chosen among full-length microtubule-binding proteins, fragments of microtubule-binding proteins, or even isolated Microtubule-Binding Domains, which are known to bind specifically to polymerized tubulin, such as microtubules.

The "Microtubule-Binding Domain" (MBD) relates to the one or more fragment(s) of a microtubule-binding protein that is/are responsible for its binding to polymerized tubulin, and in particular microtubules.

Although "Microtubule-Associated Proteins" (MAP) may be also polymerized-tubulin binding proteins and/or Microtubule-binding proteins, the expression "Microtubule-Binding Domain" (MBD) refers to a domain that is able to specifically and bind directly to microtubules. For the same reasons, a "polymerized-tubulin binding moiety" will refer to a moiety that binds specifically and directly to polymerized-tubulin.

Thus, a MBD may comprise all the possible sequences of amino acids that lead to the binding of the microtubule-binding protein to microtubules.

For reference, a Microtubule-Binding Domain of the invention may be derived from the Tau protein, such as the Tau isoform 2 (Accession Number: NP_005901.2), which includes sequence SEQ ID N°1, which includes sequences SEQ ID N°11 to 14.

A Microtubule-Binding Domain of the invention may also be derived from the MAP1A protein (Accession Number: NP_002364), which includes sequence SEQ ID N°2.

A Microtubule-Binding Domain of the invention may also be derived from the MAP2 protein (Accession Number: NP_002365), which includes sequence SEQ ID N°3.

A Microtubule-Binding Domain of the invention may also be derived from the MAP4 protein (Accession Number: AAA67361), which includes sequence SEQ ID N°4.

A Microtubule-Binding Domain of the invention may also be derived from the MAP6 protein (Accession Number: NP_149052), which includes sequence SEQ ID N°5.

A Microtubule-Binding Domain of the invention may also be derived from the EB1 protein (Accession Number: NP_036457), which includes sequence SEQ ID N°6.

Thus, a Microtubule-Binding Domain of the invention may be selected in a group comprising or consisting of: Tau of sequence SEQ ID N°1 and SEQ ID N°10 to 14, MAP1A of sequence SEQ ID N°2, MAP2 of sequence SEQ ID N°3, MAP4 of sequence SEQ ID N°4, MAP6 of sequence SEQ ID N°5, EB-1 of sequence SEQ ID N°6 and/or any Microtubule-Binding Domain that is derived from Microtubule-Associated proteins, and fragments, and combinations thereof.

Methods for identifying polymerized-tubulin binding moieties and/or microtubule-binding domains in a protein have already been reported in the Art. See for reference: Cravchik et al.; Identification of a novel microtubule-binding domain in microtubule-associated protein 1A (MAP1A). J Cell Sci, 107 (Pt 3), 661-72, 1994.

An assay for determining the sequence of putative Microtubule-Binding Domains is further provided herebelow:

The proposed procedure to test whether or not a sequence of amino acids is a "Microtubule-Binding Domain" with a Boolean answer is based on the appearance of a microtubule-like pattern by optical microscopy in cells expressing the tested amino acid sequence using direct (fluorescent tags such as GFP) or indirect labeling (antibody).

For example, spastin (accession: NP 055761), a microtubule-severing proteins, when mutated at lysine 388 to arginine (K388R) to prevent microtubule severing, binds microtubules strongly. Such sequence of amino acids can be considered as a "microtubule-binding domain". See for reference: Errico et al.; Spastin, the protein mutated in autosomal dominant hereditary spastic paraplegia, is involved in microtubule dynamics, Hum Mol Genet, 11, 153-163, 2002.

Microtubule-Binding Domains (MBP) are often found in tandems, and/or as repeats. For instance, Tau protein is a highly soluble microtubule-associated protein (MAP) for which at least six isoforms have been found in humans, and which may comprise three or four Microtubule-Binding Domains on its carboxy-terminus end.

For example, the longest tau iso form comprises four putative microtubule-binding domains (aa: 243-274; 275-305, 306-336 and 337-368. Accession NP_005901.2), respectively of sequences SEQ ID N°11-14. However the flanking regions of tau also reinforce its binding to microtubules. See for reference: Trinczek et al., Domains of tau protein, differential phosphorylation, and dynamic instability of microtubules. Mol Biol Cell, 6(12), 1887-902.

Thus, such flanking regions may also be included as an additional part of the Microtubule-Binding Domain, without departing from the scope of the invention.

Thus, a polymerized-tubulin binding moiety preferably comprises a plurality of Microtubule-Binding Domain(s), which includes Microtubule-Binding Domains in tandems and/or repeats, which also includes at least two, at least three, or even at least four Microtubule-Binding Domains. These domains can also be separated by linkers, in order to improve their binding to microtubules Microtubule-Binding Domains may be the same or different. In particular, they may be part of the same microtubule-binding protein, or from different microtubule-binding proteins. Preferably, they are are part of the same microtubule-binding protein.

According to one exemplary embodiment, a polymerized-tubulin binding moiety includes at least one fragment of Tau that binds to microtubules, which also includes at least one Tau Microtubule-Binding Domain, such as a Tau MBD of sequence SEQ ID N°1, SEQ ID N°11, SEQ ID N°12, SEQ ID N°13 and/or SEQ ID N°14, and combinations thereof.

Methods and Uses for Detecting an Interaction Between Protein Bait(s) and Candidate Prey(s)

An easy to run method to rapidly identify potential protein interactions in living and fixed eukaryotic cells, such as mammalian cells, is provided.

First, the nucleic acid sequence coding for the bait is inserted in a plasmid to be fused to a given microtubule binding domain. Then, a screening can be performed with antibodies directed against the potential endogenous partners in fixed cells or with complementary oligonucleotide to detect nucleic acid interacting-partner. This will be of interest for many laboratories interested in determining whether or not two proteins interact with each other with their commercial or home-made antibodies or with nucleic acid with dedicated nucleic sequence.

In both living and fixed cells, classical GFP-tagged plasmid encoding for a given set of preys relevant to the investigated interactions can be used to screen for potential partners of a given protein (bait) and compared with control (only tau-GFP protein for example).

This method can be used in complement with known techniques such as the classical Yeast-two hybrid (Y2H) techniques to determine whether the Y2H results were not false positives and whether the interactions indeed take place in eukaryotic cells. This will be more relevant that pull down/immuno-precipitation assay generally used in complement to Y2H data as this strategy requires cell lysis.

High throughput analysis of protein interactomes in 96-well plates in fixed or living cells is also possible. A glass bottom may be required for high resolution imaging with oil-immersed lenses (see for example Zell-Kontact GmbH; reference: 5241-20).

According to a first object, the invention relates to a method for detecting an interaction between one or more protein bait and one or more candidate prey in an eukaryotic cell, comprising the steps of:

a) providing an eukaryotic cell expressing (i) one or more protein bait, and (ii) one or more candidate prey, wherein said protein bait comprises a bait moiety and a polymerized-tubulin binding moiety, b) determining the occurrence of an interaction between said one or more protein bait and said one or more candidate prey in the eukaryotic cell, wherein said protein bait is bound to polymerized tubulin in the eukaryotic cell. Said protein bait is bound to polymerized tubulin in the eukaryotic cell, thereby localizing said one or more candidate prey along said polymerized tubulin, thereby detecting said interaction.

Advantageously, the detection of the candidate prey in the eukaryotic cell is able to generate a "microtubule-like pattern" or a "polymerized tubulin-like pattern" if (i) the candidate prey is able to interact with the protein bait, and if (ii) the protein bait is simultaneously bound to microtubules or polymerized-tubulin respectively in the eukaryotic cell.

Thus, the detection of said "microtubule-like pattern" or "polymerized tubulin-like pattern" is indicative of an interaction between said one or more protein bait and said one or more candidate prey in the eukaryotic cell.

In particular, the detection of the candidate prey in the eukaryotic cell is able to generate a "microtubule-like pattern" or "polymerized tubulin-like pattern" if (i) the candidate prey is able to interact with the bait moiety, and if (ii) the polymerized-tubulin binding moiety is simultaneously bound to microtubules or polymerized tubulin respectively in the eukaryotic cell.

Thus, according to said embodiment, the detection of said "microtubule-like pattern" or "polymerized tubulin-like pattern" is also indicative of an interaction between said one or more bait moiety and said one or more candidate prey in the eukaryotic cell.

Thus, the invention also relates to a method for detecting an interaction between one or more bait moiety and one or more candidate prey in an eukaryotic cell, comprising the steps of:

a) providing an eukaryotic cell expressing (i) one or more protein bait, and (ii) one or more candidate prey, wherein said protein bait comprises a bait moiety and a polymerized tubulin-binding moiety, b) determining the occurrence of an interaction between said one or more bait moiety and said one or more candidate prey in the eukaryotic cell, wherein said protein bait is bound to polymerized tubulin in the eukaryotic cell. Said protein bait is bound to polymerized tubulin in the eukaryotic cell, thereby localizing said one or more candidate prey along said polymerized tubulin, thereby detecting said interaction.

The one or more candidate prey may be a protein and/or a nucleic acid.

Methods and uses of the invention are suitable for detecting an interaction between one or more protein bait and one or more candidate prey, which includes one protein bait and one candidate prey, one protein bait and more than one candidate prey, and more than one protein bait and one candidate prey.

Methods of the invention are also suitable for detecting an interaction between a plurality of protein baits and a plurality of candidate preys.

According to another embodiment, the method is for detecting an interaction between one protein bait and one candidate prey in the eukaryotic cell.

According to the invention, an “eukaryotic cell” includes any eukaryotic cell that is susceptible to contain and/or express polymerized-tubulin, such as microtubules.

According to a particular embodiment, the eukaryotic cell is selected in a group comprising primary cells, stable cell lines, stem cells and Induced Pluripotent Stem cells (IPS). For example, the eukaryotic cell may be selected in a list comprising, or consisting of mammalian cells and insect cells.

In particular, the eukaryotic cell may be selected in a list comprising, or consisting of: HEK cells, NRK cells and HeLa cells, in particular NRK cells.

The cell in step b) can be a fixed cell or a living cell.

When the cell in step b) is a living cell, it is preferred that the protein bait and/or the candidate prey comprise a detectable tag such as a fluorescence tag.

The use of a living cell in step b) allows for detection of the candidate prey along dynamical polymers of tubulin, such as microtubules, when interacting with the bait.

When the cell in step b) is a fixed cell, the method requires an additional step of fixation, prior to step b). Protocols for obtaining fixed cells are well known in the Art.

In any case, microtubules appear as bright lines on fluorescence images, which renders the binding of the preys on them easily detectable by probing for instance the appearance of μm-long bright lines using the prey’s fluorescence signal, which leads to a characterizing “microtubule-like pattern”.

The candidate prey may be modified or unmodified candidate prey.

The candidate prey may also be a homologous or heterolous candidate prey.

The protein bait and/or the candidate prey may also comprise a detectable moiety. In particular, the detectable moiety may be a fluorescent protein.

The detectable moiety may be selected in a group comprising: GFP, YFP, XFP, RFP, CFP, DsRED, mCherry, Luciferase, Cyanine dyes such as Cy2 or Cy3 or Cy5, fluorescein, rhodamine, and Alexa fluor dyes.

In particular, the fluorescent protein can be selected in a group comprising: GFP, YFP, XFP, RFP, CFP, DsRED, and mCherry.

Fluorescent proteins are widely known in the Art and may be found, for instance, in Shaner & Steinbach & Tsien (A guide to choosing fluorescent proteins; Nat Methods; 2(12): 905-9; 2005).

The invention’s method provides a quick and effective answer regarding whether or not the bait and the prey are interacting within a same macromolecular complex in real time but does not necessarily tell whether or not the interaction is direct. To overcome this limitation, FRET can be performed simultaneously: the fluorescent label of the bait will be the donor while that of the prey will be the acceptor. Y2H can also be used to probe the direct interaction in a complementary experiment.

According to one embodiment, the detectable moiety is suitable for Förster resonance energy transfer (FRET).

According to one embodiment, the invention also relates to a method as defined above, which comprises a step of determining the occurence of a direct interaction between the bait and the prey using Förster resonance energy transfer (FRET) in the eukaryotic cell.

According to said embodiment, the invention also relates to a method for detecting an interaction between one or more protein bait and one or more candidate prey in an eukaryotic cell, comprising the steps of:

a) providing an eukaryotic cell expressing (i) one or more protein bait, and (ii) one or more candidate prey, wherein said protein bait comprises a bait moiety and a polymerized tubulin-binding moiety, b) determining the occurrence of an interaction between said one or more protein bait and said one or more candidate prey in the eukaryotic cell, wherein said protein bait is bound to polymerized tubulin in the eukaryotic cell, and c) determining the occurrence of a direct interaction between the protein bait and the candidate prey using Förster resonance energy transfer (FRET), wherein steps b) and c) of determining the occurrence of an interaction may be achieved in that order or in a different order. Said protein bait is bound to polymerized tubulin in the eukaryotic cell, thereby localizing said one or more candidate prey along said polymerized tubulin, thereby detecting said interaction.

According to another embodiment, the invention relates to a method as defined above, wherein in step b) determining the occurence of the said prey in the eukaryotic cell, is a detection method selected in a group comprising: binding to an antibody, hybridization with a nucleic acid, and/or fluorescence measurement.

For instance, the step b) of determining the occurence of an interaction can be achieved using videomicroscopy.

The step b) of determining the occurence of an interaction can also be achieved using a computer-assisted recognition method, such as a computer-assisted recognition method taught in Altinok et al. (Activity analysis in microtubule videos by mixture of hidden Markov models; Computer Vision and Pattern Recognition, IEEE Computer Society Conference, 2, 1662-1669; 2006).

In addition, the invention relates to a method as defined above, comprising before step b), at least one step of depolymerizing cellular tubulin using a Microtubule-Depolymerizing drug or cold exposure.

Microtubule-disrupting, Microtubule-depolymerizing or Microtubule-disassembling drugs, such as Nocodazole, Vinblastine, Vincristine, Colchicine, Colcemid, Podophyllotoxin, Rizhoxin or Vinorelbine, can also be used for that purpose.

Cold exposure is known in the Art and generally relates to a step of depolymeryzing microtubules by exposing them to low temperature. Protocols which relate to cold exposure are known in the Art, and for instance are taught in Ochoa et al. (Cold exposure reveals two populations of microtubules in pulmonary endothelia; Am. J. physiol. Lung Cell. Mol. Physiol.; 300:L132-L138; 2011).

Steps of polymerization and depolymerization as defined above may be advantageously repeated over time, leading to a succession of alternating phases of association and dissociation of the bait over time.

Thus, the invention also relates to a method for detecting an interaction between one or more protein bait and one or more candidate prey in an eukaryotic cell, comprising the steps of:

a) providing an eukaryotic cell expressing (i) one or more protein bait, and (ii) one or more candidate prey, wherein said protein bait comprises a bait moiety and a polymerized-tubulin binding moiety, b) optionally depolymerizing cellular tubulin using a Microtubule-Depolymerizing drug or cold exposure, c) optionally determining the occurence of a first interaction between said one or more protein bait and said one or more candidate prey in the eukaryotic cell, wherein said protein bait is bound to polymerized tubulin in the eukaryotic cell, d) optionally depolymerizing cellular tubulin using a Microtubule-Depolymerizing drug or cold exposure, and e) determining the occurence of a second interaction between said one or more protein bait and said one or more candidate prey in the eukaryotic cell, wherein said protein bait is bound to polymerized tubulin in the eukaryotic cell.

In step c), said protein bait is bound to polymerized tubulin in the eukaryotic cell, thereby localizing said one or more candidate prey along said polymerized tubulin, thereby detecting said first interaction.

In step e), said protein bait is bound to polymerized tubulin in the eukaryotic cell, thereby localizing said one or more candidate prey along said polymerized tubulin, thereby detecting said second interaction.

Of course, steps b) and d) of depolymerization may be repeated over time.

According to said methods, it is possible to detect not only interactions between baits and preys, but also the dynamics of polymerized-tubulin in the eukaryotic cell.

Because the bait and the prey are able to interact in a living environment, it is also an object of the invention to allow not only the detection of an interaction between the bait and the prey, but also to detect post-translational modifications that may occur in the eukaryotic cell. Thus, methods of the invention may further include a step of detecting the occurence of a post-translational modification, for instance of the bait moiety and/or of the candidate prey. Post-translational modifications are well known in the Art and include, for instance, modifications like phosphorylation events.

Thus, this method is also efficient for identifying, in real-time, post-translational events such as phosphorylation that modify bait-prey interactions, using for instance video microscopy, as detailled in the examples for eIF2B-eIF2A interactions.

The invention also relates to the use of a polymerized-tubulin binding moiety, as a tool for determining the occurence of an interaction between said one or more bait and one or more candidate prey in an eukaryotic cell. Said protein bait is bound to polymerized tubulin in the eukaryotic cell, thereby localizing said one or more candidate prey along said polymerized tubulin, thereby detecting said interaction.

In particular, the invention relates to the use of a polymerized-tubulin binding moiety fused to one or more bait, as a tool for determining the occurence of an interaction between said one or more bait and one or more candidate prey in an eukaryotic cell. Said protein bait is bound to polymerized tubulin in the eukaryotic cell, thereby localizing said one or more candidate prey along said polymerized tubulin, thereby detecting said interaction.

More particularly, the invention relates to the use of at least one Microtubule-Binding Domain fused to one or more bait, as a tool for determining the occurence of an interaction between said one or more bait and one or more candidate prey in an eukaryotic cell. Said protein bait is bound to microtubules in the eukaryotic cell, thereby localizing said one or more candidate prey along said microtubules, thereby detecting said interaction.

According to said embodiment, the invention also relates to the use of a plurality of Microtubule-Binding Domains, such as tandems of Microtubule-Binding Domains, fused to one or more bait, as a tool for determining the occurence of an interaction between said one or more bait and one or more candidate prey in an eukaryotic cell.

Preferably, the polymerized-tubulin binding moiety and/or the Microtubule-Binding Domain may be used in the form of a protein bait as disclosed further herebelow.

Protein Bait

According to a third object, the invention relates to a protein bait, either as such or that is suitable for the methods and uses as defined above.

In particular, the invention relates to a protein bait comprising (i) a polymerized-tubulin binding moiety comprising one or more Microtubule-Binding Domain (MBD), and (ii) a bait moiety.

According to some embodiments, the "bait moiety" does not interact, or co-localize, with polymerized tubulin or microtubules in the eukaryotic cell.

According to some embodiments, the bait moety may consist of antibodies or fragments thereof, or nucleic-acid binding proteins. Thus, according to some embodiments, the protein bait comprises:

a polymerized tubulin-binding moiety comprising one or more Microtubule-Binding Domain(s), and a bait moiety that does not interact with polymerized tubulin in the eukaryotic cell.

According to some embodiments, the bait moety may consist of antibodies or fragments thereof, or nucleic-acid binding proteins. Thus, according to some embodiments, the protein bait comprises:

a polymerized tubulin-binding moiety comprising one or more Microtubule-Binding Domain(s), and a bait moiety consisting of antibodies or fragments thereof or nucleic-acid binding proteins.

A barrier for interaction can be a reduction of the accessibility of the bait when fused to a polymerized tubulin-binding moiety due to the proximity of the microtubule surface. To maximize the bait's accessibility to the prey, the bait can be attached to a projection domain, which is preferably an unstructured tail allowing a nm-long spacing between the microtubule or the polymerized-tubulin surface and the bait.

Thus, according to a particular embodiment, a protein bait according to the invention comprises a polymerized tubulin-binding moiety comprising one or more Microtubule-Binding Domain (MBD), and a bait moiety.

Advantageously, the Microtubule-Binding Domains (MBD) are selected among a group comprising: Tau of sequence SEQ ID N°1, MAP1A of sequence SEQ ID N°2, MAP2 of sequence SEQ ID N°3, MAP4 of sequence SEQ ID N°4, MAP6 of sequence SEQ ID N°5, EB-1 of sequence SEQ ID N°6, or any other Microtubule-Binding Domain that is derived from Microtubule-Associated proteins, and combinations thereof.

According to some embodiments, the protein bait comprises:

a polymerized tubulin-binding moiety comprising one or more Microtubule-Binding Domain(s), selected in a group consisting of: Tau of sequence SEQ ID N°1 and SEQ ID N°10 to 14, MAP1A of sequence SEQ ID N°2, MAP2 of sequence SEQ ID N°3, MAP4 of sequence SEQ ID N°4, EB-1 of sequence SEQ ID N°6 and/or fragments, and combinations thereof; and a bait moiety.

According to some embodiments, the protein bait comprises:

a polymerized tubulin-binding moiety comprising one or more Microtubule-Binding Domain(s), selected in a group consisting of: Tau of sequence SEQ ID N°1 and SEQ ID N°10 to 14, MAP1A of sequence SEQ ID N°2, MAP2 of sequence SEQ ID N°3, MAP4 of sequence SEQ ID N°4, EB-1 of sequence SEQ ID N°6 and/or fragments, and combinations thereof; and a bait moiety that does not interact with polymerized tubulin in the eukaryotic cell.

According to some embodiments, the protein bait comprises:

a polymerized tubulin-binding moiety comprising one or more Microtubule-Binding Domain(s), selected in a group consisting of: Tau of sequence SEQ ID N°1 and SEQ ID N°10 to 14, MAP1A of sequence SEQ ID N°2, MAP2 of sequence SEQ ID N°3, MAP4 of sequence SEQ ID N°4, EB-1 of sequence SEQ ID N°6 and/or fragments, and combinations thereof; and a bait moiety consisting of antibodies or fragments thereof or nucleic-acid binding proteins.

Accordingly, the protein bait may further comprise one Linker (L) region located between the polymerized tubulin-binding moiety and the bait moiety.

A Linker (L) region is generally an unstructured domain, in particular an unstructured domain which allows a nm-long spacing between the polymerized-tubulin surface and the bait, which is critical to increase the accessibility of the bait to the prey.

Examples of Linker Regions are Known in the Art

Projection domains are found in Microtubule-Associated Proteins (MAPs) such as MAP2 or Tau, and are involved in microtubule bundling and in determining the spacing between microtubules. They may also interact with other cytoskeletal structures.

Preferably, in order to maximize the bait's accessibility to the prey, the bait is attached to a Linker region which is a projection domain from a MAP, such as Tau, or a fragment thereof.

Thus, according to a preferred embodiment, the protein bait comprises (i) a polymerized-tubulin binding moiety comprising one or more Microtubule-Binding Domain (MBD), (ii) a projection domain and (ii) a bait moiety.

A "projection domain" of the invention may comprise or consist of a N-terminal fragment of Tau.

According to a particular embodiment, a "projection domain" of the invention is the Tau projection domain of sequence SEQ ID N°9, or a fragment thereof.

The Linker region, or projection domain, can be of varying length, which includes any region or domain as defined above of from 1 to 150 amino acids in length, which includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 and 150 amino acids in length.

When the protein bait comprises (i) a polymerized-tubulin binding moiety comprising one or more Microtubule-Binding Domains and (ii) a projection domain, it is preferable that both parts are part of the same protein, in particular the same Microtubule-Associated Protein, such as Tau.

The bait moiety may or may not comprise a detectable moiety, such a fluorescent protein.

Advantageously, the protein bait may further comprise any detectable moiety as defined above, at its N-terminal or C-terminal part, such as a fluorescent label that is detectable using fluorescence microscopy.

In a non-limitative manner, the detectable moiety may be a fluorescent protein, such as a protein selected in a group comprising: GFP, YFP, XFP, RFP, CFP, DsRED, and mCherry.

Vectors and Cell Lines

The invention also relates to a vector containing an expression cassette suitable for expressing a protein bait of the invention.

Thus, a vector of the invention is suitable for expressing a protein bait of the invention, which includes vectors comprising:

an expression cassette coding for a bait moiety fused to a polymerized-tubulin binding moiety comprising one or more Microtubule-Binding Domain (MBD), or alternatively, an expression cassette coding for a polymerized-tubulin binding moiety comprising one or more Microtubule-Binding Domain (MBD) and which is directly suitable for cloning at least one bait moiety as a fused protein bait.

An expression cassette is directly suitable for cloning at least one bait moiety as a fused protein bait, according to standard cloning protocols, if it is suitable for the introduction of an insert coding for said bait moiety in frame with said polymerized-tubulin binding moiety. Standard cloning protocols include protocols comprising a step of digestion with restriction enzymes, and/or site-specific recombination.

A vector of the invention may include one, or more than one, selectable marker. A selectable marker is a marker gene introduced into a cell, especially a bacterium or cells in culture, that confers a trait suitable for artificial selection.

According to preferred embodiments, the expression cassette is coding for a polymerized-tubulin binding moiety comprising one or more Microtubule-Binding Domain (MBD) which are derived from a Microtubule-Associated Protein of the invention.

According to a most preferred embodiment, the expression cassette is coding for a polymerized-tubulin binding moiety comprising one or more Microtubule-Binding Domain (MBD) which are derived from the protein Tau of sequence SEQ ID N°10.

Vectors of the Invention, May Comprise:

an expression cassette coding for a protein library for said bait moiety fused to a polymerized-tubulin binding moiety comprising one or more Microtubule-Binding Domain (MBD), or alternatively, an expression cassette coding for a polymerized-tubulin binding moiety comprising one or more Microtubule-Binding Domain (MBD) and which is directly suitable for cloning a nucleic acid coding for a protein library for said bait moiety as a fused protein bait.

Examples of vectors which are suitable for expression in eukaryotic cells include the Gateway® pEF-Dest51 plasmid.

The invention further relates to cell lines that are transfected with a vector of the invention, and/or that stably express a protein bait of the invention.

According to another object, the invention relates to kits for detecting an interaction of one or more protein bait with one or more candidate prey in a cell, comprising a protein bait, a vector, and/or a cell line of the invention.

Thus, the invention also relates to a kit for detecting an interaction of one or more protein bait with one or more candidate prey in a cell, comprising a protein bait, a vector, and/or a cell line of the invention, and combinations thereof.

The invention also relates to a kit as defined above, comprising a nucleic acid library coding for the said bait or the said prey, and/or a protein library comprising said bait or the said prey, and/or a reagent suitable for detecting the occurence of said bait or said prey in the said cell, and combinations thereof.

Thus, the invention also relates to a kit for detecting an interaction of one or more protein bait with one or more candidate prey in an eukaryotic cell, comprising:

a vector of the invention, and/or a cell line of the invention, optionally, a protein library for one or more bait moiety, optionally, a reagent suitable for detecting the occurence of said protein bait and/or said candidate prey in an eukaryotic cell.

Thus, the invention also relates to a kit for detecting an interaction of one or more protein bait with one or more candidate prey in an eukaryotic cell, comprising:

a vector of the invention, and/or a cell line of the invention, a nucleic acid library or a protein library coding for one or more bait moiety, optionally, a reagent suitable for detecting the occurence of said protein bait and/or said candidate prey in an eukaryotic cell.

EXAMPLES

A. Material & Methods

1. Plasmid Construction of the Tau-Fused Bait.

A protein of interest is fused to a Microtubule-binding domain and to an unstructured projection domain. The longest isoform of the human tau protein (Accession number: NP_005901.2) of sequence SEQ ID N°10 is used due to the presence of an unstructured region (or projection domain) at its N-terminal part to favor bait's accessibility to prey, and to the repetition of Tau Microtubule binding domains at its C-terminal part. Sequence SEQ ID N°10 includes four microtubule-binding domains (Accession NP_005901.2: aa: 243-274; 275-305, 306-336 and 337-368, respectively of sequences SEQ ID N°11-14.

The tau gene containing at 5' end the following restriction sites: PacI, AscI and SphI was amplified by PCR and inserted in the Gateway pCR8/GW/TOPO entry plasmid (Invitrogen™). The resulting plasmid will be mentioned hereafter as the "backbone entry plasmid". YB-1 and eIF2B genes were amplified by PCR using primers containing Pad and AscI restriction sites and then inserted in pCR-Blunt II-TOPO plasmid (Invitrogen™).

GFP and RFP genes were amplified by PCR using primers containing AscI and SphI restriction sites and then inserted in pCR-Blunt II-TOPO plasmid (Invitrogen™) using standard protocols. The plasmids containing all the above mentioned genes were propagated and purified by Mini Kit (Thermo Scientific, reference K0503) and the inserted genes were verified by sequencing. YB-1 and eIF2B genes inserted in pCR-Blunt II-TOPO plasmid were digested with PacI and AscI. GFP and RFP genes inserted in pCR-Blunt II-TOPO plasmid were digested with AscI and SphI.

Ligation was performed in order to insert the above mentioned genes into the backbone entry plasmid, previously digested with the same restriction enzymes (PacI, AscI and SphI).

The following entry plasmids were generated:

GFP-tau-pCR8/GW/TOPO
YB-1-tau-pCR8/GW/TOPO
YB-1-GFP-tau-pCR8/GW/TOPO
YB-1-RFP-tau-pCR8/GW/TOPO
eIF2B-tau-pCR8/GW/TOPO
eIF2B-RFP-tau-pCR8/GW/TOPO The LR recombination reactions (Invitrogen™) were also performed according to the manufacturer's protocol in order to transfer the genes of interest from the backbone entry plasmids into the Gateway® pEF-Dest51 plasmid suitable for protein expression in eukaryotic cells.

Thus, the following expression plasmids were also generated:

GFP-tau-pEF-Dest51
YB-1-tau-pEF-Dest51
YB-1-GFP-tau-pEF-Dest51
YB-1-RFP-tau-pEF-Dest51
eIF2B-tau-pEF-Dest51
eIF2B-RFP-tau-pEF-Dest51

The eIF2a-GFP fragment was amplified by PCR and inserted in pcDNA3.3 TOPO TA plasmid (Invitrogen™)

2. Fixed Cell Preparations.

Cells growing on coverslips were washed with PBS and fixed with cold methanol for 15 min at −20° C. After fixation, cells were washed in PBS and incubated for 1 hour in blocking solution. Cells were then incubated for 1 hour with primary antibodies, washed extensively in PBS and incubated with fluorochrome-coupled secondary antibodies in blocking solution. After final washes with PBS, samples were prepared for fluorescence microscopy analysis. Methanol fixation was preferred because it better reveals microtubule structures.

3. Videomicroscopy of Living Cells.

Cells were transiently transfected with the indicated expression vectors and then cultured for 24 h before real-time monitoring of microtubules. Fluorescence videomicroscopy was implemented on an inverted microscope (Axiovert 220; Carl Zeiss MicroImaging, Inc). GFP emission was detected with a 63×/1.4 NA objective. Time-lapse images were captured at 4 s intervals using a cooled CCD camera (Zeiss).

Cells grown on glass bottom multiwell plates (Zell-Kontakt GmbH) can be analyzed automatically for high throughput applications using high-content cell analyzer (example: BD Pathway TM855, preferably used with oil immersed lenses to obtain higher resolution). The detection with a boolean output (interaction or no interaction) can be followed up using a computer-assisted recognition method.

B. Results

Example 1. General Protocol for High-Throughput Analysis and Detection System 1) The cDNA sequences encoding for a known protein or a polypeptide chain called "bait" are inserted in a plasmid which directs, within the cell the synthesis of this bait fused to a microtubule binding protein (tau, MAP2) or domain linked to a projection domain to favor bait's accessibility to prey. The bait can additionally be fused to fluorescent label like a fluorescent protein (GFP, RFP, . . . ).

2) cDNA sequences encoding the "prey", a polypeptide or protein, are inserted in a plasmid to direct its expression within cell. The prey is possibly fused to a fluorescent label such as a fluorescent protein (i.e. GFP or XFP) for its detection in living cells via fluorescence microscopy.

3) Array of cell samples in 6 to 96-well plates are co-transfected with different preys (see FIG. 1) to identify various interacting partners for given bait at high throughput. An automatic detection system allows the recognition of the preys bound to microtubules so in order to obtain a Boolean output (interacting or not interacting).

Figure 2:
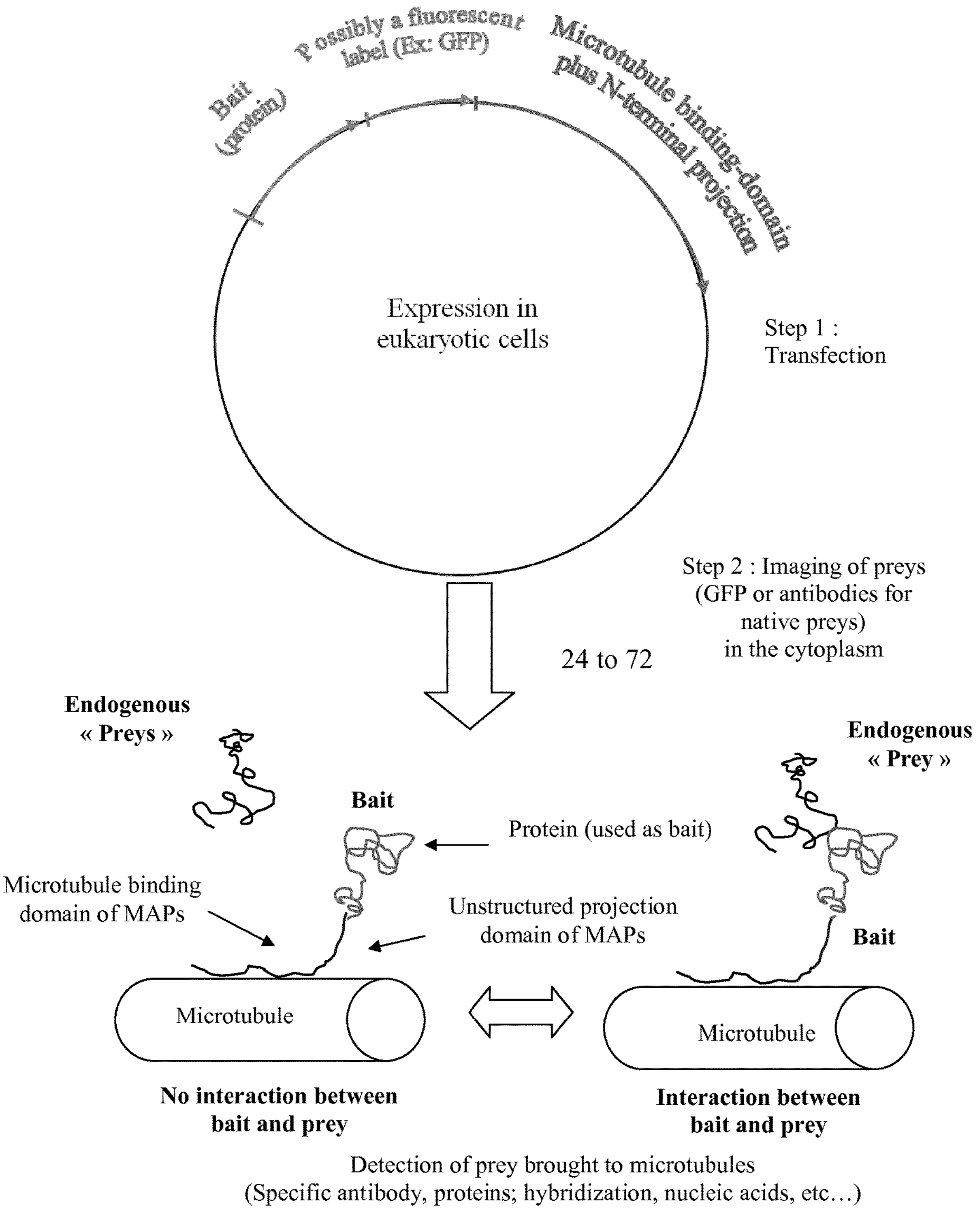
FIG. 2: Principle of the method for fixed cells and for an endogenous prey. Detection of an endogenous prey brought to microtubules, in two steps. A first step (Step 1) includes the transfection of an expression vector coding for a protein bait comprising a Microtubule binding domain and optionally a fluorescent label. A second step (Step 2) includes the detection of the endogenous prey using reagents such as antibodies directed against the native prey or hybridization with nucleic acids. The prey is then detected on the microtubules after its interaction with the bait.
Figure 3:
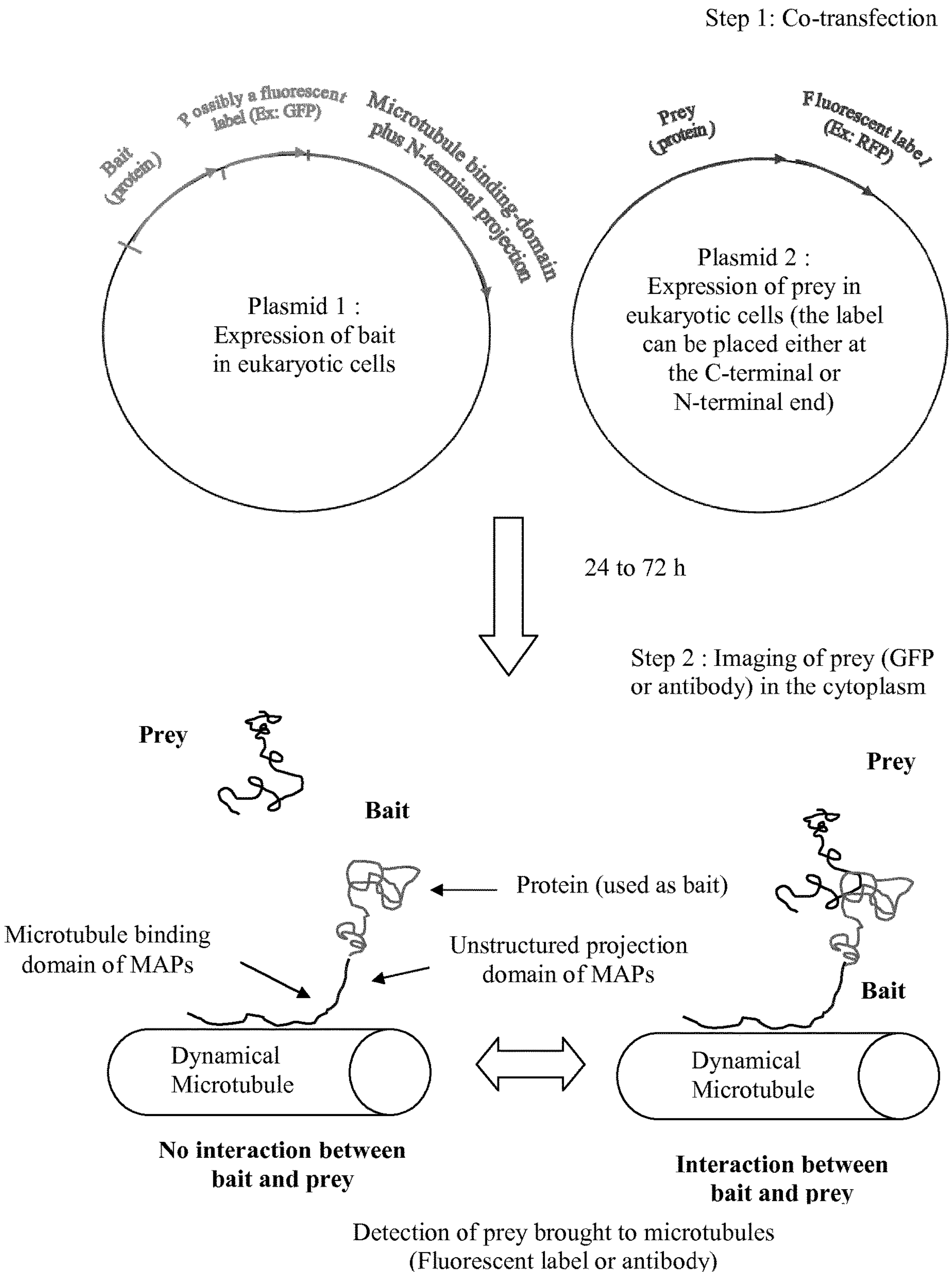
FIG. 3: Principle of the method for living cells and for an exogenous prey. A first step (Step 1) includes the co-transfection of two expression vectors; a first plasmid expresses a protein bait comprising a Microtubule binding domain and optionally a fluorescent label. A second plasmid expresses the exogenous prey optionally labelled with a fluorescent label. A second step (Step 2) includes the detection of the exogenous prey along dynamic microtubules or in the cytoplasm using a fluorescent label specific for the prey and/or an antibody.

4) Detection:

i) For detection in living or fixed cells (FIGS. 2 and 3), the co-expression of fluorescent bait and prey allows the detection by fluorescent videomicroscopy of the prey along dynamical microtubules, when interacting with the bait. Time lapse imaging for less than 1 minute (15 images per minute) is sufficient to detect microtubule structures with a high sensitivity. The sensitivity in living cells is enhanced compared to fixed cells since the highly dynamical microtubules can allow the detection of preys bound to the baits via differential fluorescence images of the prey (image at time t0 minus images at time t0+Δt, (Desforges et al.; An intercellular polyamine transfer via gap junctions regulates proliferation and response to stress in epithelial cells. Mol Biol Cell 24, 1529-1543; 2013), a classical technique to highlight microtubule movements which is useful here to withdraw the fluorescence background of non-interacting preys.

To better improve the accessibility of bait to prey and the sensitivity of detection, one can depolymerize microtubules in living cells, using reversible drugs like nocodazole, which allows the bait to explore freely the cytoplasm and to interact with the bait away from the microtubule surface. Then, once the microtubule-depolymerizing drug is washed out, microtubules rapidly regrow from the centrosome (<2 min), such a pattern being captured by videomicroscopy using the prey's fluorescence whenever an interaction between the bait and prey takes place. Confocal fluorescence microscopy or Total internal fluorescence microscopy (TIRF) can be used to enhance the sensitivity by reducing the fluorescence signal to noise ratio.

ii) For detection in fixed cells (FIG. 3), the method allows the detection by fluorescence of native preys (endogenous proteins, endogenous RNA or other biomolecules) brought to microtubules thanks to their interaction with the bait. Detection can be done using classical optical fluorescence microscopy after labeling of the prey with specific antibodies (proteins chosen for being potentially interacting with the bait and using negative controls) or after in situ hybridization when the aim is to detect interaction of nucleic acids with the bait (RNA in particular including miRNA and mRNA). This option is also relevant when prey's fluorescent label (GFP, RFP or other labels) may hinder the prey-bait interactions or when prey over-expression may bias the results.

For detection in fixed cells co-expressing bait and fluorescent preys, fluorescent detection of preys brought to microtubules due to their interaction with the bait can be performed directly using classical optical microscope due to its fluorescent label.

In any case, microtubules appear as bright lines on fluorescence images, which renders the binding of the preys on them easily detectable by probing the appearance of μm-long bright lines using the prey's fluorescence signal.

iii) Stable cell lines expressing the bait can also be used to improve the efficiency of co-expression and to facilitate the investigations of the interaction of a given protein bait. If the bait expression is toxic, an inducible expression system can be proposed in a stably transfected cell line to obtain at a given time a significant expression.

iv) A dual FRET labeling (CFP label for the bait and YFP label for the prey, for example) can be implemented to simultaneously detect whether bait and target interacting within the same macromolecular complexes (prey brought to microtubules) are directly bound to each other in this complex (FRET signal).

Example 2. Detection of YB-1 Self-Attraction and YB-1 Binding to cy3-Labeled-Poly-T-Probes in Fixed and Living NRK Cells YB-1 (Accession number: NP_004550.2) is known to be one of the core mRNA-binding proteins (Nekrasov et al., The mRNA-binding protein YB-1 (p50) prevents association of the eukaryotic initiation factor eIF4G with mRNA and inhibits protein synthesis at the initiation stage. J Biol Chem 278, 13936-13943; 2003). We then investigated whether or not mRNA molecules can be brought to microtubules using YB-1-tau as bait (FIG. 1C).

In FIG. 1C we show NRK cells transfected with the human YB-1 protein, an mRNA binding protein, fused to tau and GFP. The bait, YB-1-GFP-tau, was then indeed detected on microtubules in the GFP fluorescence image, in contrast to YB-1-GFP or endogenous YB-1 which remained dispersed in the cytoplasm.

mRNA molecules were clearly detected on microtubules using in situ hybridization (cy3-labeled poly-T probes) on transfected and fixed cells but not on those which didn't express YB-1-tau. This result validates that YB-1 fused to tau and brought to microtubules is able to interact with mRNA.

Another property of YB-1 is that it interacts with itself as shown via two hybrid screening (Ashizuka et al.; Novel translational control through an iron-responsive element by interaction of multifunctional protein YB-1 and IRP2. Mol Cell Biol 22, 6375-6383; 2002). We probe for such interaction in fixed cells using YB-1-GFP as a prey and YB-1-tau as a bait.

In FIG. 4B, NRK cells were transfected with the YB-1-tau plasmid without GFP label. The bait, YB-1-tau, is brought to microtubules, as clearly observed using anti-YB-1 labeling (FIG. 4B, both endogenous YB-1 and YB-1 fused to tau are then detected in this case).

Figure 4:
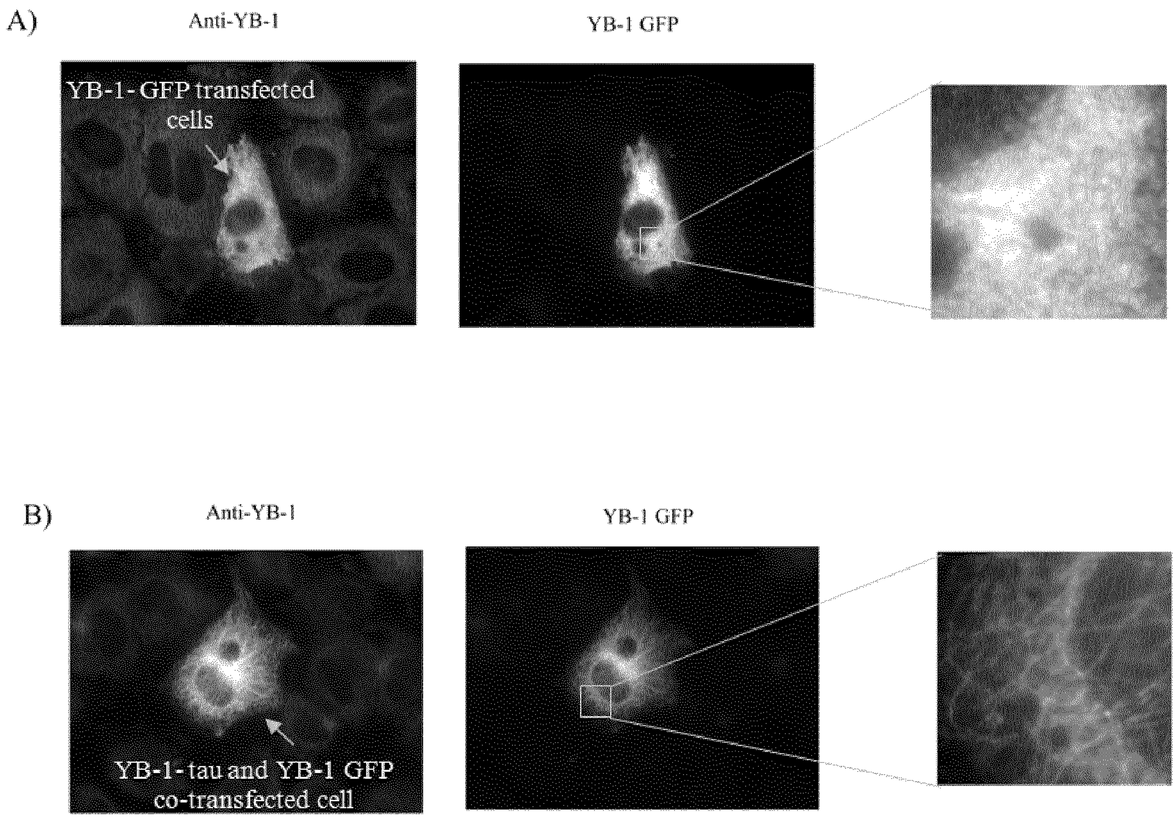
FIG. 4: Protein-protein interaction (YB-1 self-attraction) detected using the method in fixed cells. (A) NRK cells are transfected with a plasmid coding for YB-1-GFP showing the random distribution of this protein in the cytoplasm. (B) NRK cells are cotransfected with plasmids encoding for YB-1-tau (Bait) and YB-1-GFP (prey). YB-1 is known to be a self-attracting protein and YB-1-GFP is brought to microtubules due to its binding to the bait. Left panel: Visualization with an anti YB-1. Middle panel: Visualization of YB-1 GFP only. Right Panel: close-view of microtubules binding to the bait from the middle panel.
Figure 5:
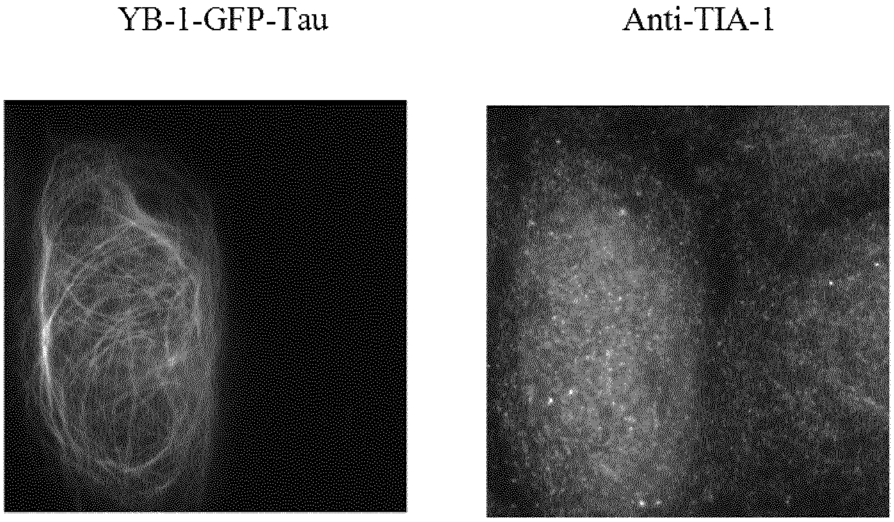
FIG. 5: YB-1 is not interacting with TIA-1 in fixed cells. (left panel) NRK cells are transfected with a plasmid coding for YB-1-GFP-tau. (right panel) TIA-1 location is probed using a specific anti-TIA-1 antibody. No interaction is observed between the bait and TIA-1. This is a negative control.

Thus, we found that GFP-YB-1 is attracted on microtubules in the presence of YB-1-tau (FIG. 4). As a negative control, we observed whether another mRNA binding protein, TIA-1, which is not reported to interact with YB-1 would, using our method, cocalize with microtubules. Results show that TIA-1 does not colocalize with microtubules using YB-1-tau as a bait, thus in agreement with the expected non interaction between the two proteins, at least under the present condition (FIG. 5).

Figure 7:
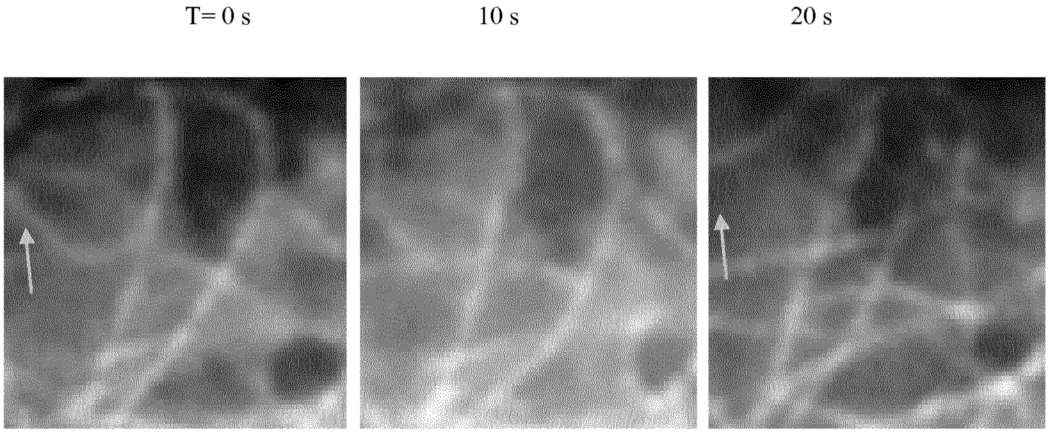
FIG. 7: Video-microscopy imaging of YB-1-GFP brought to microtubules due to its binding to YB-1-tau in living NRK cells. Microtubules movements can be observed (see arrows) over time (from left to right: T=0 s; 10 s; 20 s), which improves the sensitivity of the detection, after removal of background by differential imaging.

NRK cells were also co-transfected with YB-1-tau (bait) and YB-1-GFP (prey). Video-microscopy of living cells revealed the appearance of dynamical microtubular structures (FIG. 7), which are not present in cells transfected with YB-1-GFP only. This experiment thus allows to detect protein interaction in real time and to use microtubule dynamics as tool to improve the sensitivity of detection.

Example 3. Detection of Binding of eIF2A to eIF2B After eIF2A Phosphorylation in Living Cells In FIG. 6A, in HeLa cells transfected with eIF2B-tau, eIF2B-tau is bound to microtubules as clearly observed using anti-eiF2B labeling.

One of the early responses in mammalian cells exposed to environmental stress (hyperthermia, osmotic stress, hypoxia, oxidative stress, virus) is to block the initiation of translation. Such initiation block is mediated by the phosphorylation of the initiation factor eIF2A via various kinases like PKR and PERK. This phosphorylation occurs at serine 51 and leads to the strong binding of eIF2A to eIF2B. The formation of this complex prevents the regeneration of eIF2A-GDP (GDP/GTP regeneration) by eIF2B (Krishnamoorthy et al.; Tight binding of the phosphorylated alpha subunit of initiation factor 2 (eIF2alpha) to the regulatory subunits of guanine nucleotide exchange factor eIF2B is required for inhibition of translation initiation. Mol Cell Biol 21, 5018-5030; 2001).

The point is that eIF2A is in large excess compared to eIF2B, so that, even if a small fraction of eIF2A is phopshorylated, no free eIF2B are then available for recycling eIF2a due to the binding of phosphorylated eIF2A to eIF2B.

Figure 6:
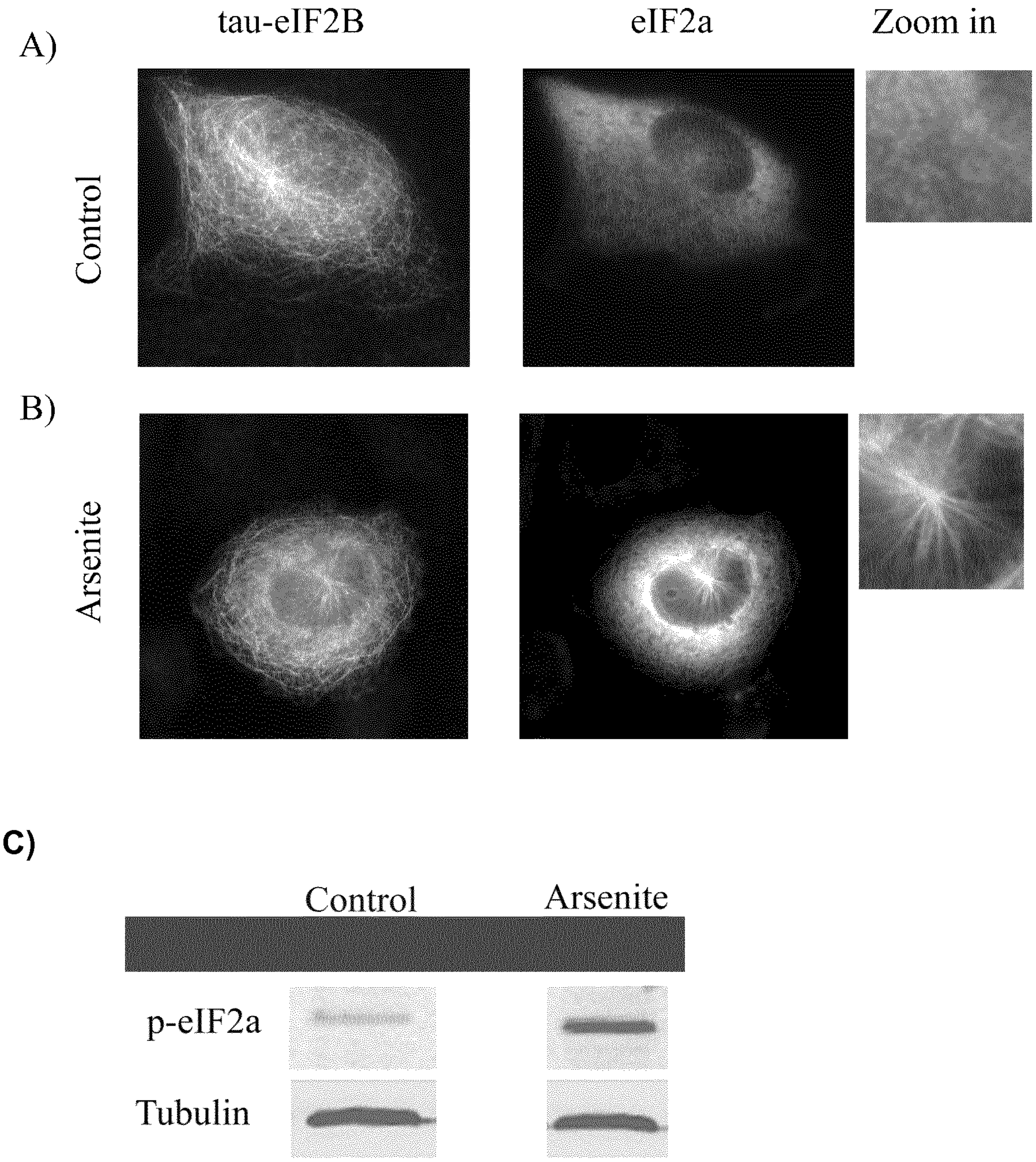
FIG. 6: Detection of the binding to eIF2B of phosphorylated eIF2A in HeLa cells. Cells were transfected with a plasmid encoding for eIF2B-tau (bait) and eiF2a-GFP (prey) under the following conditions. (A) Control: eiF2A-GFP is not significantly interacting with eIF2B-tau. (B) After stress (0.5 mM arsenite for 45 minutes), eiF2A is phosphorylated which leads to an interaction with eIF2B-tau (localized on microtubules). Microtubular structures can be easily detected. (C) Western blot of NRK cells after arsenite treatment showing the phosphorylation of eIF2A (anti-eIF2A). anti-tubulin (loading control)

We took advantage of this critical stress signal to detect the binding of eIF2A to eIF2B after stress using living human HeLa cells co-transfected with tau-eIF2B (the human c subunit) and eIf2A-GFP. In the absence of stress, the interaction of eIF2a-GFP with the bait is not noticeable since eIF2A is homogenously distributed in the cytoplasm (FIG. 6A). In contrast, after arsenite treatment (used to induce the phosphorylation of eIF2A-GFP), eIF2A-GFP is clearly detected on microtubules, which demonstrates that the bait is interacting with the prey (FIG. 6B, eIF2B-tau). As a control, phosphorylation of eIF2A upon arsenite treatment is shown by western-blot.

Figure 8:
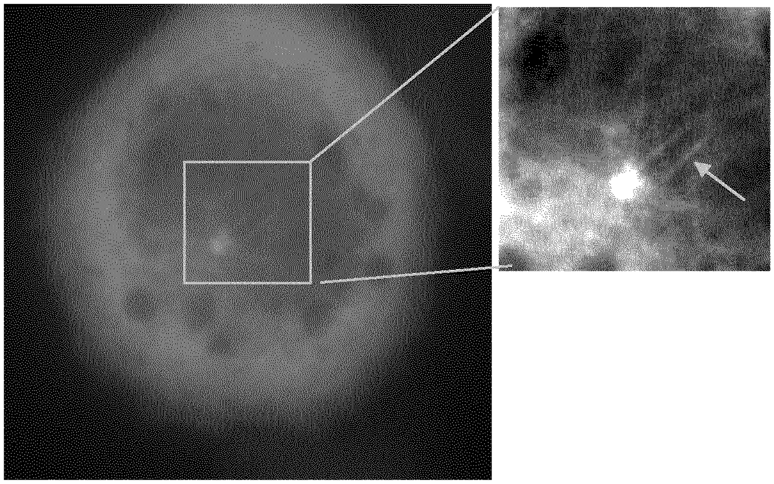
FIG. 8: Videomicroscopy imaging of eIF2A-GFP brought to microtubules due to its binding to eIF2B after arsenite stress in HeLa cells. Arsenite treatment triggers the phosphorylation of eIF2A-GFP, and thus its binding to eIF2B. Microtubules are indirectly detected (see arrow in the higher magnification image).

We also detected in living cell the interaction of eIF2A with eIF2B after arsenite treatment to trigger the phosphorylation of eIF2A and thus its binding to eIF2B. For this purpose, HeLa cells were co-transfected with eIF2B-tau (bait) and eIF2A-GFP (prey) and exposed to 0.5 mM arsenite for 30 min (FIG. 8).

Example 4. Image Analysis and Statistics

Cells were co-transfected and analyzed after 36 h when expressing both bait and prey tagged with two different fluorescent labels, RFP and GFP, respectively. Only cells with a healthy appearance were selected for the statistics.

We paid attention to obtain optimal resolution conditions and to select cells in which microtubules were clearly distinguished using bait fluorescence as signal. For the same series of experiment, we used the same objective lens (100×/1.4 NA or 65×/1.4 NA for fixed and living cells respectively). At this stage, we analyzed whether, although using achromatic lenses, the red and green images were not shifted with respect to each other. Such shift, if any, can be corrected using the ImageJ's Plug-In, "Align RGB planes".

To quantify the colocalization level between a protein bait fused to tau and putative protein preys, we adapted a method previously described in French et al. (Colocalization of fluorescent markers in confocal microscope images of plant cells. Nature protocols, 3, 619-628; 2008). Both images were then filtered using a FFT high pass filter to remove spatial frequencies which are not relevant to microtubule structures (larger structures than 5 μm). Images of the bait and the prey were then merged into a single green-red image. Then, the ImageJ's plug-in, "PSC Co-localization", was used to measure the spearman's coefficient, in three different region of interest (ROI) for the same cell where microtubules are clearly observed in the bait image. The area of the ROI was fixed (225 $\mu m^2$) to avoid any bias due to the surface considered to measure the correlation coefficient. We controlled that all the experimental results presented in this article were reproducible by performing each experiment in triplicates. To extrapolate the value of the spearman coefficient at the zero expression level of the protein bait, we used the least square method and a linear curve fitting.

The spearman coefficient is a better choice than the closely-related Pearson coefficient because it includes non-linear relationship. Fluorescence intensity may indeed not increase linearly with the number of protein baits or preys, especially when short-ranged non radiative interactions take place on microtubules at elevated bait or prey surface densities.

Example 5. Microtubule Regrowth Assay

Cells were placed on ice for 30 min to totally dissociate microtubule into tubulin dimers and warmed-up at 37° C. in the presence of 300 nM nocodazole. Nocodazole was then washed out from the culture medium. After nocodazole removal, denovo microtubule elongation started from the centrosomal area.

Example 6. Quantification of Co-Localization Between and Prey on Microtubules Images of bait and prey florescence, here YBRFP-Tau and YB-1-GFP, obtained from fixed cells, were first spatially filtered by using Fast Fourier Transform. Low spatial frequencies, corresponding to feature larger than 2 μm, were discarded. Microtubules structures then appeared clearly in the images of the protein bait and, provided that co-localization occurs, in the images of the prey protein. Images of the bait and the prey were merged and proceed using the 'Pearson-Spearman Correlation Co-localization' plug-in for ImageJ.

The measured correlation coefficient is very sensitive to the alignment of the bait and prey fluorescence images. When images are shifted, the ImageJ's plug in, 'Align RGB planes', can be used to correct the shift, which results in an increase of the spearman coefficient representative of the colocalization between YB-1-GFP and YB-1-RFP-Tau.

SEQUENCE LISTING

SEQ ID No 1. Tau microtubule binding sequence:151-400, Accession: NP_005901.2):
```
IATPRGAAPPGQKGQANATRIPAKTPPAPKTPPSSGEPPKSGDRSGYSSP
GSPGTPGSRSRTPSLPTPPTREPKKVAVVRTPPKSPSSAKSRLQTAPVPM
PDLKNVKSKIGSTENLKHQPGGGKVQIINKKLDLSNVQSKCGSKDNIKHV
PGGGSVQIVYKPVDLSKVTSKCGSLGNIHHKPGGGQVEVKSEKLDFKDRV
QSKIGSLDNITHVPGGGNKKIETHKLTFRENAKAKTDHGAEIVYKSPVVS
```

SEQ ID No 2. MAP1A (aa:282-630, Accession: NP_002364):
```
QNKILEGLEKLRHLDFLRYPVATQKDLASGAVPTNLKPSKIKQRADSKES
LKATTKTAVSKLAKREEVVEEGAKEARSELAKELAKTEKKAKESSEKPPE
KPAKPERVKESSEALKAEKRKLIKDKVGKKHLKEKISKLEEKKDKEKKEI
KKERKELKKDEGREEKKDAKKEEKRKDTKPELKKISKPDLKPFTPEVRKT
LYKAKVPGRVKIDRSRAIGEKELSSEPQTPPAQKGTVPLPTISGHRELVL
SSPEDLTQDFEEMKREERALLAEQDTGLGDKPFPLDTAEEGPPSTAIQGT
PPSVPGLGQEEHVMKEKELVPEVPEEQGSKDRGLDSGAETEEEKDTWEEK
KQRE
```

SEQ ID No 3. MAP2 (aa:1519-1828, Accession: NP_002365):
```
FKQAKDKVSDGVTKSPEKRSSLPRPSSILPPRRGVSGDRDENSFSLNSSI
SSSARRTTRSEPIRRAGKSGTSTPTTPGSTAITPGTPPSYSSRTPGTPGT
PSYPRTPHTPGTPKSAILVPSEKKVAIIRTPPKSPATPKQLRLINQPLPD
LKNVKSKIGSTDNIKYQPKGGQVQIVTKKIDLSHVTSKCGSLKNIRHRPG
GGRVKIESVKLDFKEKAQAKVGSLDNAHHVPGGGNVKIDSQKLNFREHAK
ARVDHGAEIITQSPGRSSVASPRRLSNVSSSGSINLLESPQLATLAEDVT
AALAKQGL
```

SEQ ID No 4. MAP4 (aa:923-1084, Accession: AAA67361):
```
LATNTSAPDLKNVRSKVGSTENIKHQPGGGRAKVEKKTEAAATTRKPESN
AVTKTAGPIASAQKQPAGKVQIVSKKVSYSHIQSKCGSKDNIKHVPGGGN
VQIQNKKVDISKVSSKCGSKANIKHKPGGGDVKIESQKLNFKEKAQAKVG
SLDNVGHLPAGG
```

-continued

SEQUENCE LISTING

SEQ ID No 5. MAP6 (aa:118-321, Accession: NP_149052):
SVMRQDYRAWKVQRPEPSCRPRSEYQPSDAPFERETQYQKDFRAWPLPRR
GDHPWIPKPVQISAASQASAPILGAPKRRPQSQERWPVQAAAEAREQEAA
PGGAGGLAAGKASGADERDTRRKAGPAWIVRRAEGLGHEQTPLPAAQAQV
QATGPEAGRGRAAADALNRQIREEVASAVSSSYRNEFRAWTDIKPVKPIK
AKP SEQ ID No 6. EB1 (aa: 124-268, Accession: NP_036457):
YDPVAARQGQETAVAPSLVAPALNKPKKPLTSSSAAPQRPISTQRTAAAP
KAGPGVVRKNPGVGNGDDEAAELMQQVNVLKLTVEDLEKERDFYFGKLRN
IELICQENEGENDPVLQRIVDILYATDEGFVIPDEGGPQEEQEEY SEQ ID No 7. Alpha tubulin (Accession: AAA91576):
MRECISIHVGQAGVQIGNACWELYCLEHGIQPDGQMPSDKTIGGGDDSFN
TFFSETGAGKHVPRAVFVDLEPTVIDEVRTGTYRQLFHPEQLITGKEDAA
NNYARGHYTIGKEIIDLVLDRIRKLADQCTRLQGFLVFHSFGGGTGSGFT
SLLMERLSVDYGKKSKLEFSIYPAPQVSTAVVEPYNSILTTHTTLEHSDC
AFMVDNEAIYDICRRNLDIERPTYTNLNRLISQIVSSITASLRFDGALNV
DLTEFQTNLVPYPRIHFPLATYAPVISAEKAYHEQLSVADITNACFEPAN
QMVKCDPGHGKYMACCLLYRGDVVPKDVNAAIATIKTKRTIQFVDWCPTG
FKVGINYQPPTVVPGGDLAKVQRAVCMLSNTTAIAEAWARLDHKFDLMYA
KRAFVHWYVGEGMEEGEFSEAREDMAALEKDYEEVGVDSVEGEGEEEGEE
Y SEQ ID No 8. Beta tubulin (aa: 124-268, Accession: AAB59507):
MREIVHIQAGQCGNQIGAKFWEVISDEHGIDPTGTYHGDSDLQLDRISVY
YNEATGGKYVPRAILVDLEPGTMDSVRSGPFGQIFRPDNFVFGQSGAGNN
WAKGHYTEGAELVDSVLDVVRKEAESCDCLQGFQLTHSLGGGTGSGMGTL
LISKIREEYPDRIMNTFSVVPSPKVSDTVVEPYNATLSVHQLVENTDETY
CIDNEALYDICFRTLRLTTPTYGDLNHLVSGTMECVTTCLRFPGQLNADL
RKLAVNMVPFPRLHFFMPGFAPLTSRGSQQYRALTVPDLTQQVFDAKNMM
AACDPRHGRYLTVAAVFRGRMSMKEVDEQMLNVQNKNSSYFVEWIPNNVK
TAVCDIPPRGLKMAVTFIGNSTAIQELFKRISEQFTAMFRRKAFLHWYTG
EGMDEMEFTEAESNMNDLVSEYQQYQDATAEEEEDFGEEAEEEA SEQ ID No 9. Tau projection domain (aa: 1-150, Accession: NP_005901.2):
MAEPRQEFEVMEDHAGTYGLGDRKDQGGYTMHQDQEGDTDAGLKESPLQT
PTEDGSEEPGSETSDAKSTPTAEDVTAPLVDEGAPGKQAAAQPHTEIPEG
TTAEEAGIGDTPSLEDEAAGHVTQARMVSKSKDGTGSDDKKAKGADGKTK SEQ ID No 10. Tau (Accession: NP_005901.2):
MAEPRQEFEVMEDHAGTYGLGDRKDQGGYTMHQDQEGDTDAGLKESPLQT
PTEDGSEEPGSETSDAKSTPTAEDVTAPLVDEGAPGKQAAAQPHTEIPEG
TTAEEAGIGDTPSLEDEAAGHVTQARMVSKSKDGTGSDDKKAKGADGKTK
IATPRGAAPPGQKGQANATRIPAKTPPAPKTPPSSGEPPKSGDRSGYSSP
GSPGTPGSRSRTPSLPTPPTREPKKVAVVRTPPKSPSSAKSRLQTAPVPM
PDLKNVKSKIGSTENLKHQPGGGKVQIINKKLDLSNVQSKCGSKDNIKHV
PGGGSVQIVYKPVDLSKVTSKCGSLGNIHHKPGGGQVEVKSEKLDFKDRV
QSKIGSLDNITHVPGGGNKKIETHKLTFRENAKAKTDHGAEIVYKSPVVS
GDTSPRHLSNVSSTGSIDMVDSPQLATLADEVSASLAKQGL SEQ ID No 11. Tau MBD1aa : 243-274:
LQTAPVPMPDLKNVKSKIGSTENLKHQPGGGK SEQ ID No 12. Tau MBD2 aa : 275-305:
VQIINKKLDLSNVQSKCGSKDNIKHVPGGGS SEQ ID No 13. Tau MBD3 aa : 306-336:
VQIVYKPVDLSKVTSKCGSLGNIHHKPGGGQ SEQ ID No 14. Tau MBD4 aa : 337-368:
VEVKSEKLDFKDRVQSKIGSLDNITHVPGGGN

The invention claimed is:

1. A method for detecting an interaction between one or more protein bait and one or more candidate prey in an eukaryotic cell, comprising the steps of:

a) providing an eukaryotic cell expressing (i) one or more protein bait, and (ii) one or more candidate prey, wherein said protein bait comprises a bait moiety and a polymerized tubulin-binding moiety, and wherein the one or more protein bait binds to polymerized tubulin within the eukaryotic cell via the polymerized tubulin-binding moiety, and b) detecting an interaction between said one or more protein bait and said one or more candidate prey in the eukaryotic cell by detecting the binding of the candidate prey to the bait moiety of the one or more protein bait localized along the polymerized tubulin.

2. The method according to claim 1, wherein said one or more protein bait comprises:

a polymerized tubulin-binding moiety comprising one or more Microtubule-Binding Domain (MBD), and a bait moiety.

3. The method according to claim 2, wherein the Microtubule-Binding Domain is selected from the group consisting of: Tau of sequence SEQ ID N°1 and SEQ ID N°10 to 14, MAP1A of sequence SEQ ID N°2, MAP2 of sequence SEQ ID N°3, MAP4 of sequence SEQ ID N°4, MAP6 of sequence SEQ ID N°5, EB-1 of sequence SEQ ID N°6 and/or any Microtubule-Binding Domain that is derived from Microtubule-Associated proteins, and fragments, and combinations thereof.

4. The method according to claim 1, wherein said one or more protein bait comprises one Linker (L) region located between the polymerized-tubulin binding moiety and the bait moiety.

5. The method according to claim 1, wherein the one or more candidate prey comprises a fluorescent protein.

6. The method according to claim 1, wherein step b) includes one or more of binding to an antibody, hybridization with a nucleic acid, and fluorescence measurement.

7. The method according to claim 1, further comprising before step b), a step of depolymerizing cellular tubulin using a Microtubule-Depolymerizing drug or cold exposure.

8. The method according to claim 1, wherein the eukaryotic cell is a fixed cell or a living cell.

9. The method according to claim 1, wherein the bait moiety and/or the candidate prey is selected from the group consisting of: a protein, a peptide, a nucleic-acid binding moiety and a nucleic acid.

10. The method according to claim 9, wherein the nucleic-acid binding moiety is a nucleic-acid binding protein.

11. The method of according to claim 9, wherein the protein is an antibody.

12. The method according to claim 1, wherein the candidate prey is a nucleic acid.

13. The method according to claim 1, wherein the bait moiety and the candidate prey are different.

14. The method according to claim 1, wherein the candidate prey is heterologous.

15. The method according to claim 1, wherein the bait moiety is a nucleic-acid binding moiety and the candidate prey is a nucleic acid.

16. The method according to claim 1, wherein the bait moiety is an antibody or a fragment thereof and the candidate prey is a protein or a peptide.

17. The method according to claim 1, wherein the bait moiety is a nucleic acid and the candidate prey is a nucleic-acid binding moiety.

* * * * *